US006919958B2

(12) United States Patent
Stanke et al.

(10) Patent No.: US 6,919,958 B2
(45) Date of Patent: Jul. 19, 2005

(54) WAFER METROLOGY APPARATUS AND METHOD

(75) Inventors: Fred E. Stanke, Cupertino, CA (US); Clinton B. Carlisle, Palo Alto, CA (US); Hung Van Pham, San Jose, CA (US); Edric Tong, Sunnyvale, CA (US); Douglas E. Ruth, Sunnyvale, CA (US); James M. Cahill, Jr., San Jose, CA (US); Michael Weber-Grabau, Sunnyvale, CA (US); Elliot Burke, Goleta, CA (US); Adam E. Norton, Palo Alto, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 10/397,917

(22) Filed: Mar. 26, 2003

(65) Prior Publication Data

US 2003/0184742 A1 Oct. 2, 2003

Related U.S. Application Data

(63) Continuation of application No. 09/613,176, filed on Jul. 10, 2000, now Pat. No. 6,563,586, which is a continuation-in-part of application No. 09/533,613, filed on Mar. 22, 2000, which is a continuation of application No. 09/495,821, filed on Feb. 1, 2000, now Pat. No. 6,690,473.
(60) Provisional application No. 60/143,199, filed on Jul. 9, 1999, provisional application No. 60/125,462, filed on Mar. 22, 1999, and provisional application No. 60/118,217, filed on Feb. 1, 1999.

(51) Int. Cl.[7] .............................................. G01N 21/88
(52) U.S. Cl. .................................................. 356/237.2
(58) Field of Search .......................... 356/237.1, 237.2, 356/237.3, 237.4, 237.5

(56) References Cited

U.S. PATENT DOCUMENTS

| 3,827,811 A | 8/1974 | Kato et al. ................... 356/432 |
| 4,659,220 A | 4/1987 | Bronte et al. ................ 356/237 |
| 4,790,664 A | 12/1988 | Saito et al. .................. 356/432 |
| 5,030,008 A | * 7/1991 | Scott et al. .................. 356/394 |
| 5,125,741 A | 6/1992 | Okada et al. ............. 356/237.2 |
| 5,479,252 A | 12/1995 | Worster et al. .......... 356/237.5 |
| 5,604,344 A | 2/1997 | Finarov .................... 250/201.3 |
| 5,724,131 A | 3/1998 | Chim et al. .............. 356/237.1 |
| 5,747,813 A | 5/1998 | Norton et al. .............. 250/372 |
| 5,825,498 A | 10/1998 | Thakur et al. .............. 356/394 |
| 5,835,225 A | 11/1998 | Thakur ........................ 356/381 |
| 5,844,684 A | * 12/1998 | Maris et al. ................. 356/432 |
| 5,910,842 A | * 6/1999 | Piwonka-Corle et al. ... 356/369 |
| 5,963,314 A | * 10/1999 | Worster et al. .......... 356/237.2 |
| 6,108,091 A | 8/2000 | Pecen et al. ................. 356/381 |
| 6,108,092 A | 8/2000 | Sandhu ....................... 356/381 |
| 6,142,855 A | 11/2000 | Nyui et al. ................... 451/67 |
| 6,215,549 B1 | 4/2001 | Suzuki et al. ............... 356/445 |
| 6,310,689 B1 | * 10/2001 | Ishikawa et al. ............ 356/446 |

FOREIGN PATENT DOCUMENTS

| EP | 0 881 484 A2 | 2/1998 | .......... G01N/21/00 |
| GB | 2 314 037 A | 12/1997 | ............ B23Q/1/36 |
| WO | WO 98/37404 | 8/1998 | .......... G01N/21/00 |
| WO | WO 99/01797 | 1/1999 | ............. G03F/7/20 |

* cited by examiner

Primary Examiner—Richard A. Rosenberger
(74) Attorney, Agent, or Firm—Stallman & Pollock LLP

(57) ABSTRACT

This invention is an apparatus for imaging metrology, which in particular embodiments may be integrated with a processor station such that a metrology station is apart from but coupled to a process station. The metrology station is provided with a first imaging camera with a first field of view containing the measurement region. Alternate embodiments include a second imaging camera with a second field of view. Preferred embodiments comprise a broadband ultraviolet light source, although other embodiments may have a visible or near infrared light source of broad or narrow optical bandwidth. Embodiments including a broad bandwidth source typically include a spectrograph, or an imaging spectrograph. Particular embodiments may include curved, reflective optics or a measurement region wetted by a liquid. In a typical embodiment, the metrology station and the measurement region are configured to have 4 degrees of freedom of movement relative to each other.

3 Claims, 17 Drawing Sheets

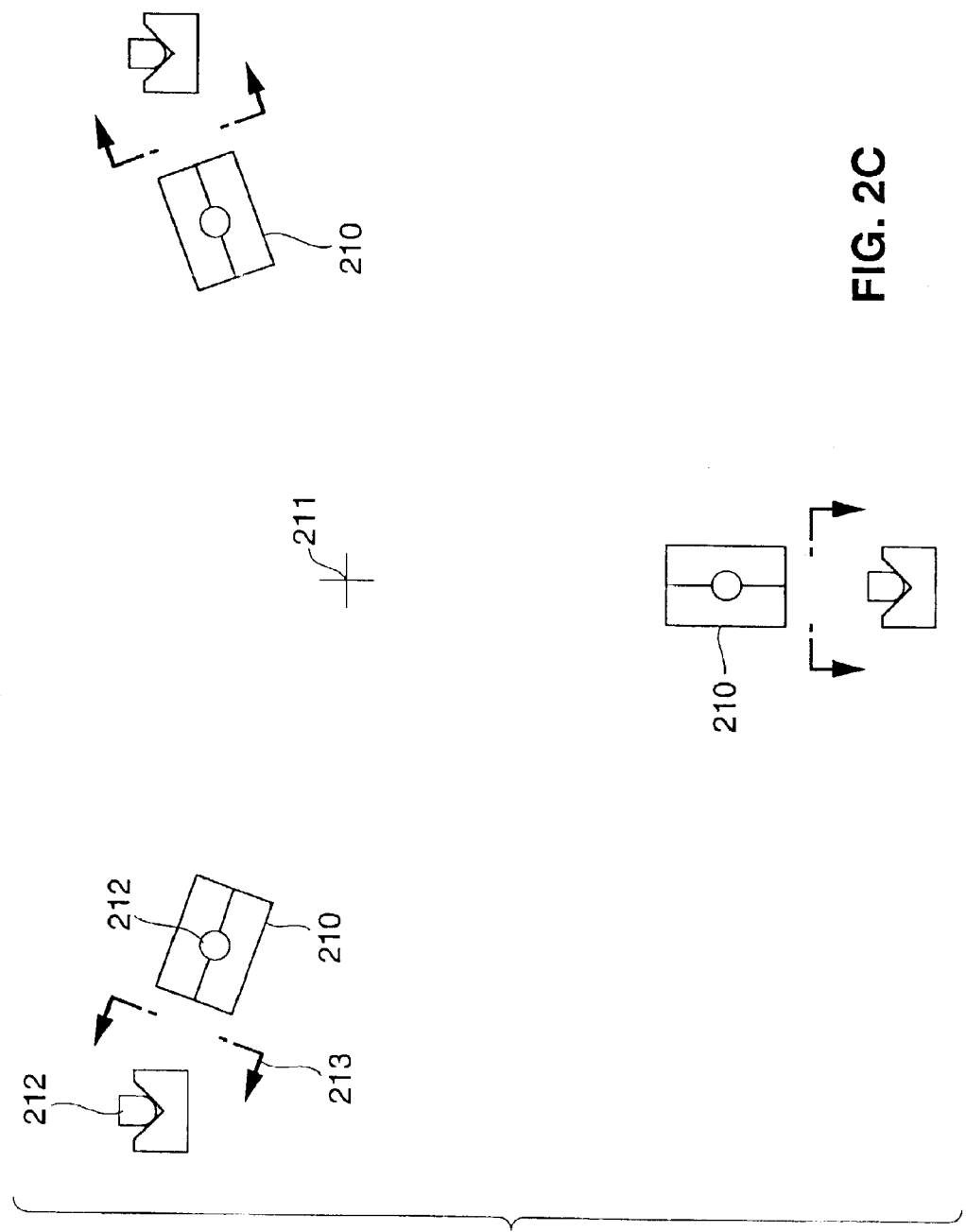

WAFER METROLOGY APPARATUS AND METHOD

CROSS REFERENCE TO RELATED APPLICATIONS

This application claims the benefit of priority to Provisional Application No. 60/143,199, filed Jul. 9, 1999, and is a continuation of U.S. applicatiion Ser. No. 09/613,176, filed Jul. 10, 2000, is now U.S. Pat. No. 6,563,586, which is a continuation-in-part of U.S. application Ser. No. 09/533,613, filed Mar. 22, 2000, which in turn claims priority to Provisional Application No. 60/118,217, filed Feb. 1, 1999, and U.S. Provisional Application No. 60/125,462, filed Mar. 22, 1999, and continuation of U.S. Application No. 09/495,821, filed Feb. 1, 2000 now U.S. Pat. No. 6,690,473, all of which are incorporated herein in their entirety by reference.

BACKGROUND OF THE INVENTION

1. Field of the Invention

This invention relates to the field of optical metrology in general, and to in-line thin-film reflectometry and profilometry for semiconductor wafers in particular.

2. Description of Related Art

A trend towards smaller critical dimension sizes in integrated circuits (IC) drives advances in technology for semiconductor capital equipment. Both technical factors, such as the ratio of the critical dimension size to the wavelengths of light used by fabrication device components, and well-known economic factors, such as wafer throughput, Cost-Of-Ownership (COO) and Overall Equipment Effectiveness (OEE) are critical.

In IC fabrication, hundreds of process steps are necessary. During some of these steps, successive layers of materials are deposited on a substrate. Subsequently, Chemical Mechanical Polishing (CMP) is often used to make a film layer planar to high degree of precision. After a CMP process step, the thickness of the remaining film may be determined to verify that it is within desired tolerances.

Optical methods are commonly used to determine the thickness of thin films since light is generally non-destructive and non-invasive. Measured optical properties of the surface or measured wave-optics effects due to the interaction of light with thin films residing on the wafer yield desired information, such as film thickness. Thus, as critical dimensions on the wafer are reduced, there is a need for advances in optical metrology to obtain required precision and accuracy.

Technical requirements of precision and accuracy must be consonant with economic requirements. Fabrication machines must process wafers at a rapid rate with high uniformity and high reliability in addition to high precision. Since the fabrication must take place in a strictly controlled environment, the size of the machine is also an important factor. Easy operation is also important, despite the complexity of the processing and measurements. Performance in terms of these and other economic factors can be expressed through figures-of-merit such as COO and OEE Wafer metrology art comprises mostly "metrology mainframe" devices, which are devices only partially integrated with an IC fabrication line. There are at least two significant problems associated with partially integrated or non-integrated metrology control. First, waiting for test measurements from metrology mainframe systems to confirm the results from each process step is inherently inefficient. Second, with a partially integrated or non-integrated unit, process engineers face difficulties in achieving and maintaining optimal process parameters once they have the measurement information.

These and other problems associated with off-line metrology result in growing need for integrated (in-line) metrology in IC wafer fabrication. With in-line devices, the metrology apparatus is physically placed within the process equipment itself. This enables a substantial reduction in times required to perform metrology measurements and shortens feedback or feedforward times between the metrology system and the process controls. By measuring critical parameters as each wafer is processed, the process equipment has information on the most recently processed wafer without stopping production. This results in good wafer-to-wafer control. Integrated metrology also significantly reduces operating costs by reducing the requirement for expensive test wafers, speeding up process qualifications and maintenance schedules, and provides an overall reduction in scrap wafers.

Related art in integrated thin-film metrology is limited regarding combining precise and accurate thin-film thickness measurements while meeting the other requirements of the semiconductor industry. Typically, related art in-line devices are limited to measurements of films of about 80 nm thickness. However, there is a need in the industry to measure film thickness of only a few tens of nanometers. Further, related art in-line devices are limited in their ability to make rapid, successive measurements over the totality of a wafer's surface.

What is needed is an imaging metrology system with rapid optical access to the entirety of a wafer surface. From the foregoing, it can be readily appreciated that many processes used in microelectronics manufacturing could benefit from integrated metrology, including but not limited to CMP, plasma etching, chemical vapor deposition, and lithography.

SUMMARY OF INVENTION

This invention is an apparatus for imaging metrology. One object is to integrate an imaging metrology station with a processor station such that the metrology station is apart from but coupled to the process station.

In one embodiment, a metrology device is provided with a first imaging camera with a first field of view containing the measurement region. Alternate embodiments include a second imaging camera with a second field of view. Preferred embodiments comprise a broadband ultraviolet light source, although other embodiments may have a visible or near infrared light source of broad or narrow optical bandwidth. Embodiments including a broad bandwidth source typically include a spectrograph, or an imaging spectrograph. Particular embodiments may include curved, reflective optics or a measurement region wetted by a liquid. In a typical embodiment, the metrology station and the measurement region are configured to have 4 degrees of freedom of movement relative to each other.

BRIEF DESCRIPTION OF THE FIGURES

FIG. 2c illustrates an alternate chuck-positioning embodiment.

DETAILED DESCRIPTION

Figure 1:
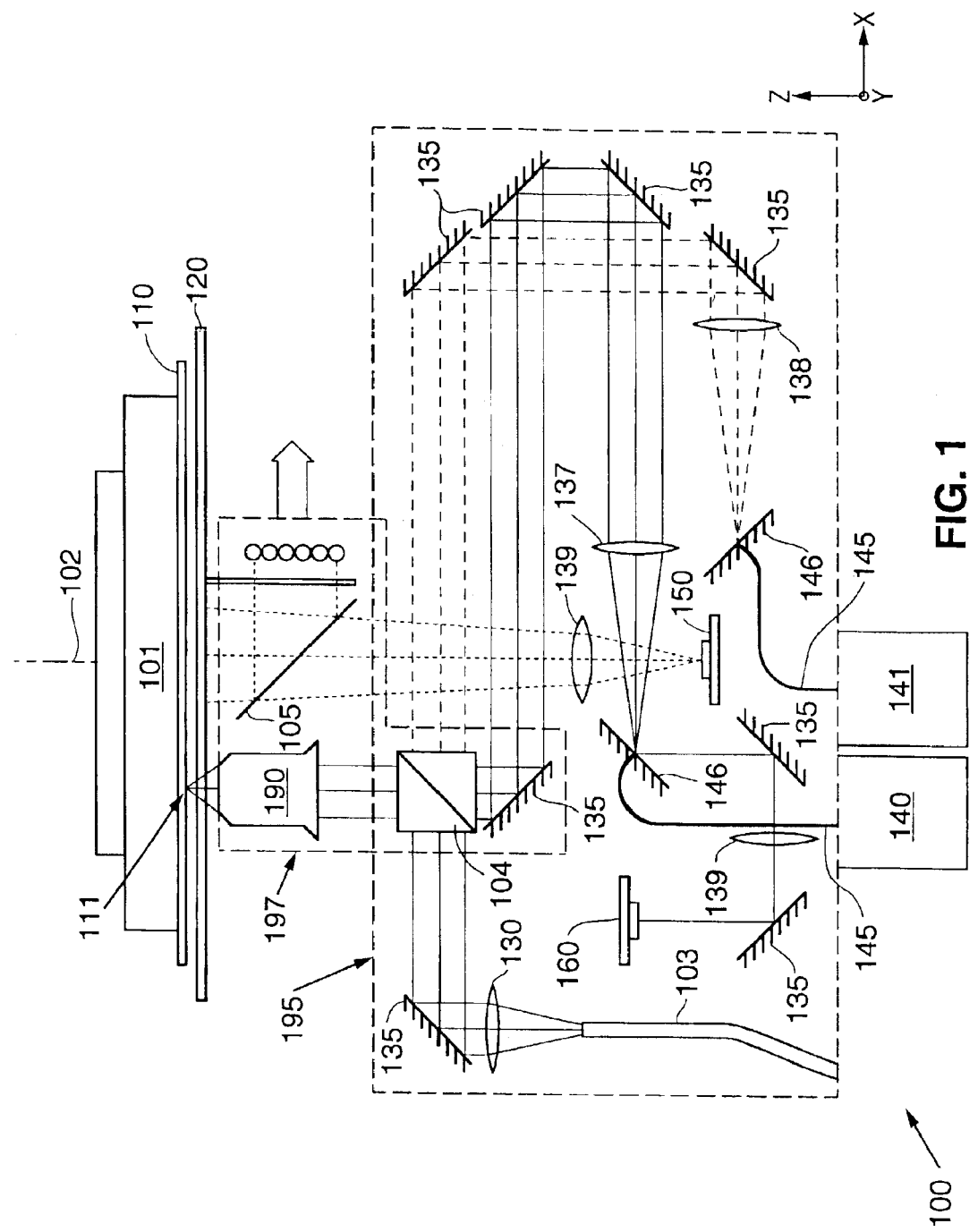
FIG. 1 shows a hardware overview for one embodiment of the wafer metrology device.

FIG. 1 illustrates one embodiment of an imaging metrology device. In FIG. 1, reflectometer assembly 100, vacuum chuck 101, vacuum chuck symmetry-axis 102, light source fiber 103, first beam splitter 104, second beam splitter 105, semiconductor wafer 110, measurement region 111, window 120, collimator 130, relay optics 135, first imaging optical assembly 137, second imaging optical assembly 138, third imaging optical assembly 139, spectrographs (including calibration filters) 140 and 141, spectrograph fiber optic 145, pinhole mirrors 146, large field-of-view camera 150, small field-of-view camera 160, auto-focusing objective lens assembly 190, first optics breadboard 195, and second optics breadboard 197 are shown. The embodiment shown in FIG. 1 may be integrated as a subsystem into a process device (not shown) or in other embodiments may be a stand-alone mainframe. Other embodiments may include other diagnostic assemblies without departing from the invention, as described below.

In FIG. 1, semiconductor wafer 110 is coupled to vacuum chuck 101, whose center-of-mass is fixed relative to the laboratory and the semiconductor wafer coupled to it. However, rotation of the vacuum chuck about the vacuum chuck symmetry-axis 102 is allowed. Reflectometer assembly 100 comprises window 120 and first and second optics breadboards 195 and 197, respectively. First optics breadboard 195 is free to translate along the y-axis, and may be driven by a direct-drive actuator in a particular embodiment. Second optics breadboard 197 is coupled to the first optics breadboard, however, the second optics breadboard is free to translate relative to the first optics breadboard along the x-axis. Objective lens assembly 190 is attached to the second optics breadboard, however, it is free to translate along the z-axis as controlled by an auto-focus system known to the art. Thus, the embodiment shown in FIG. 1 has four degrees of freedom of movement: translation along the (x, y, z) axes; and rotation of the vacuum chuck about the vacuum chuck symmetry-axis. This allows rapid optical access to the entirety of the wafer surface.

In the embodiment shown in FIG. 1, all optical elements except those on second optics breadboard 197 are coupled to and fixed relative to first optics breadboard 195. Objective lens assembly 190, are coupled to second optics breadboard 197. Thus, the objective lens assembly is free to translate along the x-axis. In addition, the objective lens assembly may be focused on semiconductor wafer 110 by translation along the z-axis. Note that translations of the first and second optics breadboards along the x-axis and y-axis allow access to the full wafer surface. Rotation of the wafer coupled to the vacuum chuck may be used in combination with translations of the first and second optics breadboards along the x and y axes to allow more rapid measurement access over the entire surface of the semiconductor wafer or to eliminate obstructions. Complete coverage of a 200 mm diameter wafer is possible with straightforward scaling to 300 mm and larger diameter wafers.

In FIG. 1, vacuum chuck 101 not only holds wafer 110 but also flattens it. This enables more accurate auto-focus, and reduces measurement errors and uncertainties due to wafer tilt and associated variations in optical path length.

Figure 2A:
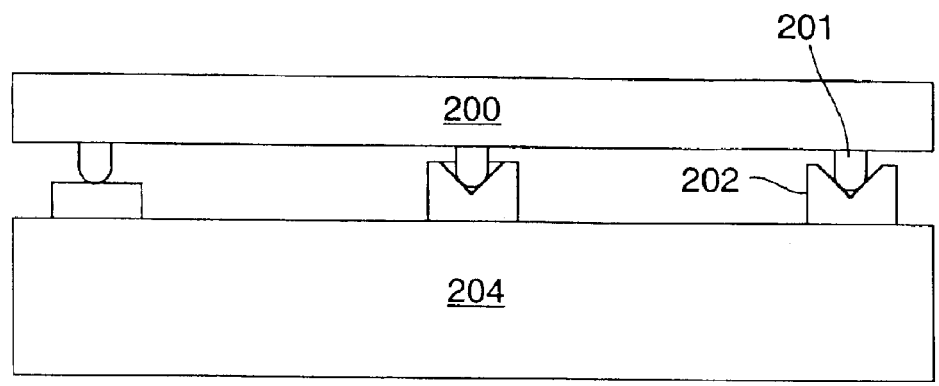
FIG. 2a illustrates one chuck-positioning embodiment with the chuck in a lowered position.
Figure 2B:
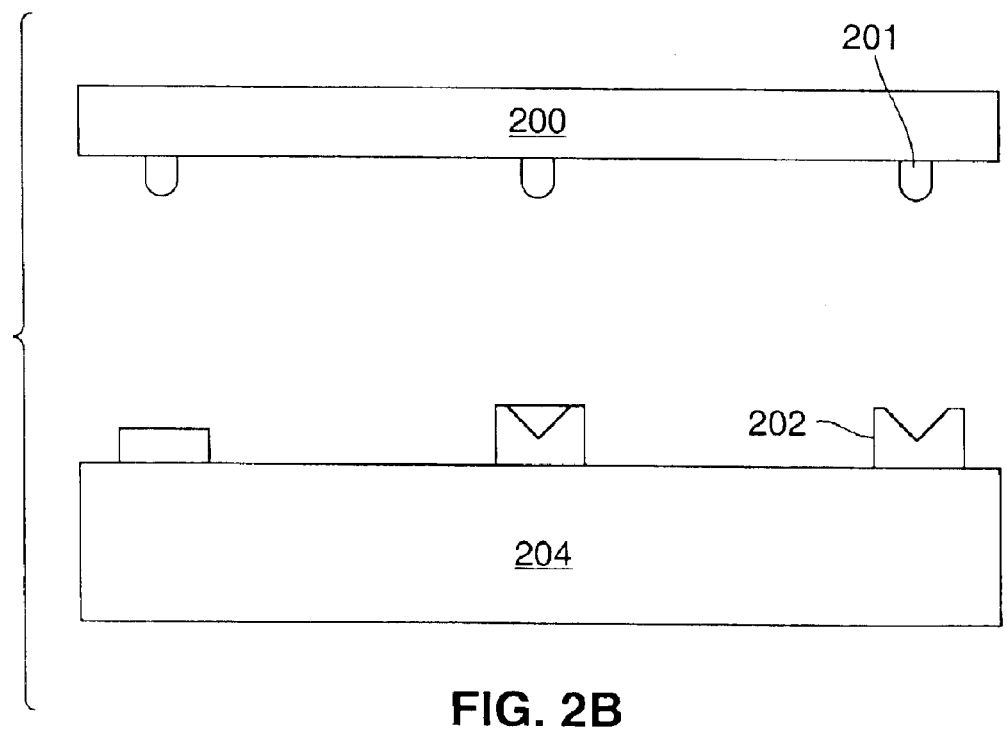
FIG. 2b illustrates one chuck-positioning embodiment with the chuck in a raised position.

FIG. 2a and FIG. 2b illustrate chuck and wafer placement for an embodiment. A lowered position is shown in FIG. 2a. The chuck raises to allow wafers to be loaded and unloaded, as shown in FIG. 2b.

In FIG. 2a, chuck assembly 200, in its lowered position, rests on the main unit through three kinematic mounts, each of which consist of a ball block 201 and a support block 202. The ball blocks are rigidly attached to the chuck assembly 200, and the support blocks are rigidly attached to the main unit 204. In an embodiment, the ball blocks are threaded into the chuck assembly to allow for height adjustment and leveling of the chuck assembly to the main unit, and there is facility to lock the adjustment in place. Other adjustment schemes are possible. The purpose of the kinematic mounts is to yield a repeatable resting position of the chuck every time it is lowered.

FIG. 2c shows an alternate embodiment. This embodiment includes supports that are three vee-blocks 210, which is a global top view with three local cross sectional views. The vees have their axes aligned to cross substantially at a single center point 211. In the absence of friction and wear, this arrangement yields only one stable lowered position, with each ball block 212 seated in its appropriate vee block, as shown in cross section 213. Since there is only one stable position, it is repeatable.

Figure 2D:
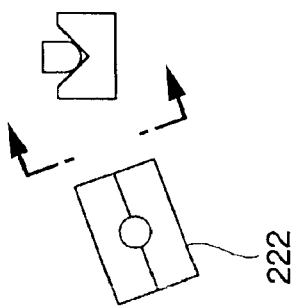
FIG. 2d illustrates a second alternate chuck-positioning embodiment.
Figure 2D:
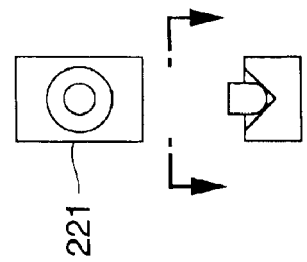
Figure 2D:
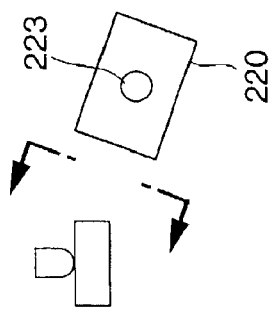

FIG. 2d shows another alternate embodiment. In this embodiment, there are three different support blocks: a flat 220, a cone 221 and a vee 222. Both of these arrangements are tolerant of imprecise mounting locations of the support blocks on the main unit and the ball blocks on the chuck assembly. As a counter-example, if two or three cone blocks are used, the distances between the support blocks on the main unit and the distances between the ball blocks on the chuck assembly must be identical to avoid ambiguity of which ball should be firmly seated in its cone.

The kinematic mounts of the above-described embodiments rely on low friction between ball blocks and support blocks, and low wear of all blocks in order to provide repeatable positioning. Friction could prevent a ball from settling to the bottom of a vee or cone, and thus yield positioning uncertainty. Wear of any of the blocks would impact the settled position of the chuck assembly. A preferred material for the supports is Zirconia ceramic, due to its extreme hardness and excellent friction and wear properties. Other hard metallic and ceramic materials are also possible in alternate embodiments. Fluid lubrication is also possible in further embodiments.

Figure 3A:
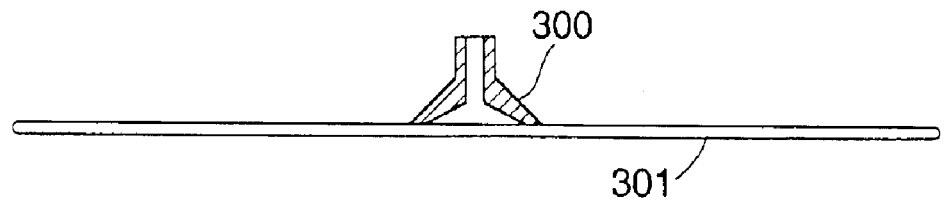
FIG. 3a illustrates a prior art wafer-gripping device.
Figure 3B:
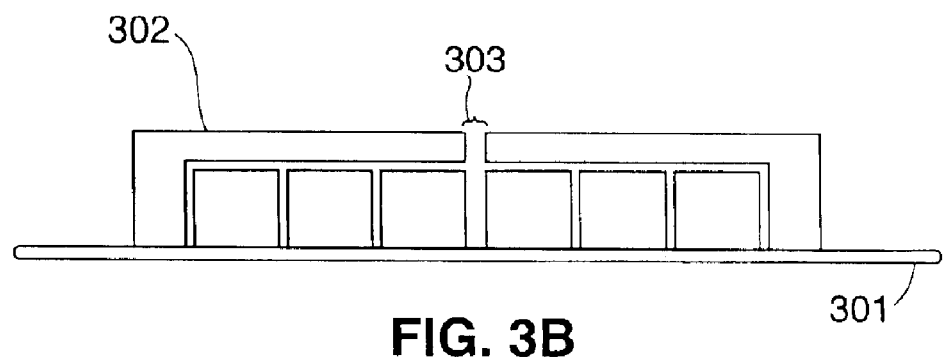
FIG. 3b illustrates a wafer chuck.

In the prior art, as shown in FIG. 3a, a vacuum wand 300 holds the wafer 301, with a vacuum applied to the channel in the center of the wand. In contrast, FIG. 3b shows an embodiment of the present invention. In FIG. 3b, vacuum chuck 302 holds the wafer 301 flat during measurement. In operation, the wafer may be mechanically placed in contact with the chuck while vacuum is applied to the pneumatic channel 303. The wafer seals the channel, and the resulting vacuum holds the wafer. The wafer is de-chucked by applying pressure to the channel instead of vacuum.

In an embodiment of the present invention, a large, flat chuck contacts the wafer over a large area, shown in FIG. 3b. The large area may be desired to maintain flatness of the wafer. A potential disadvantage of this approach may be that surface tension of water at the wafer/chuck interface may prevent the wafer from de-chucking, even when there is pressure applied to the vacuum-pressure channel. The pressurized air may form channels in the water that is holding the wafer to the chuck, and escape, without the wafer dropping.

Figure 3C:
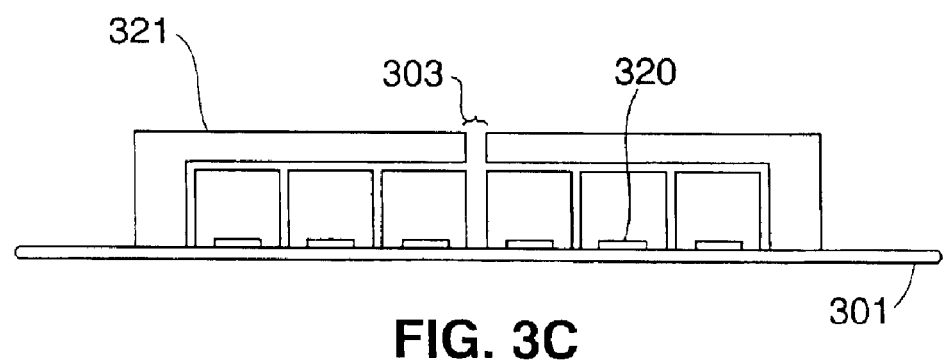
FIG. 3c illustrates an embodiment of a reduced surface area wafer chuck in cross-section.
Figure 3D:
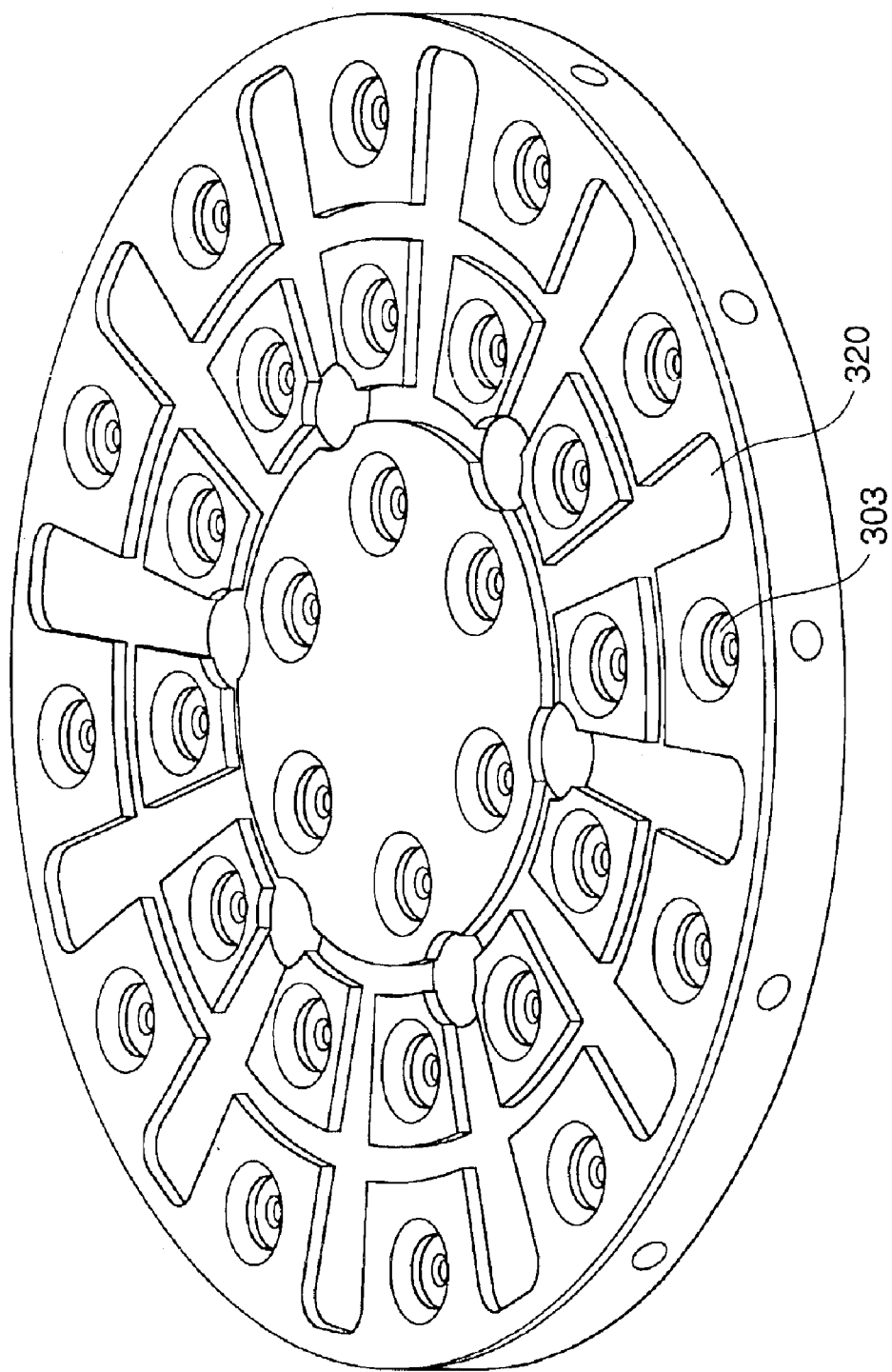
FIG. 3d illustrates an embodiment of a reduced surface area wafer chuck in perspective.

FIG. 3c shows a preferred embodiment of a reduced surface area chuck. The overall extent of the chuck may be the same as in FIG. 3b, but the area-reduction channels 320 reduce the contact area. The vacuum is applied to the wafer on pedestals between these channels, which hold the wafer flat over a large proportion of its area. The reduction in actual contact area reduces the force of water holding the wafer to the chuck, so that pressure applied to the vacuum-pressure channel will de-chuck the wafer. The reduced area chuck relies on the stiffness of the wafer to maintain local flatness, and contacts distributed over a large area to maintain global flatness. FIG. 3d shows a view of the bottom face of a reduced surface area chuck.

In preferred embodiments, a vacuum/pressure sensor senses the pressure in the pneumatic channel 303 (see FIG. 3c). The chuck uses vacuum and pressurized air to chuck and release the wafer. Whether or not the wafer is chucked or released at a given time is important information for maintaining the safety of the wafer(s) and the proper operation of the instrument. If the wafer is not in the state that is intended, the measurements may be corrupted, pattern recognition may fail, or robot conflicts may occur. Vacuum and pressure sensing in the chuck's pneumatic channels gives useful information to the controlling computer about the state of the wafer. In the following description, pressure is measured relative to atmospheric, with negative pressure signifying vacuum.

During chucking the pressure in the pneumatic channel 303 (see FIG. 3c) should be, x1<p<x2, where x1 and x2 are both negative values. If p is outside of the range, a system fault results. If x1>p, there is more vacuum than expected. This could result if the vacuum/pressure channel is blocked before vacuum reaches the wafer. This threshold will only exist if there is some leakage of vacuum at the chuck/wafer interface in normal operation. Introducing a vacuum leak near the wafer could insure this. If p>x2, there is not enough vacuum, indicating either a fault in the vacuum source, or that the wafer is not in sufficient proximity to the chuck to seal the vacuum.

During de-chucking, the pressure in the pneumatic channel 303 (see FIG. 3c) should be, x3<p<x4, where x3 and x4 are both positive values. If x3>p, there is a fault in the pressure supply. If p>x4, there is too much pressure, indicating either that the pressure vacuum pressure line is blocked, or the wafer 301 is not de-chucked.

Figure 9:
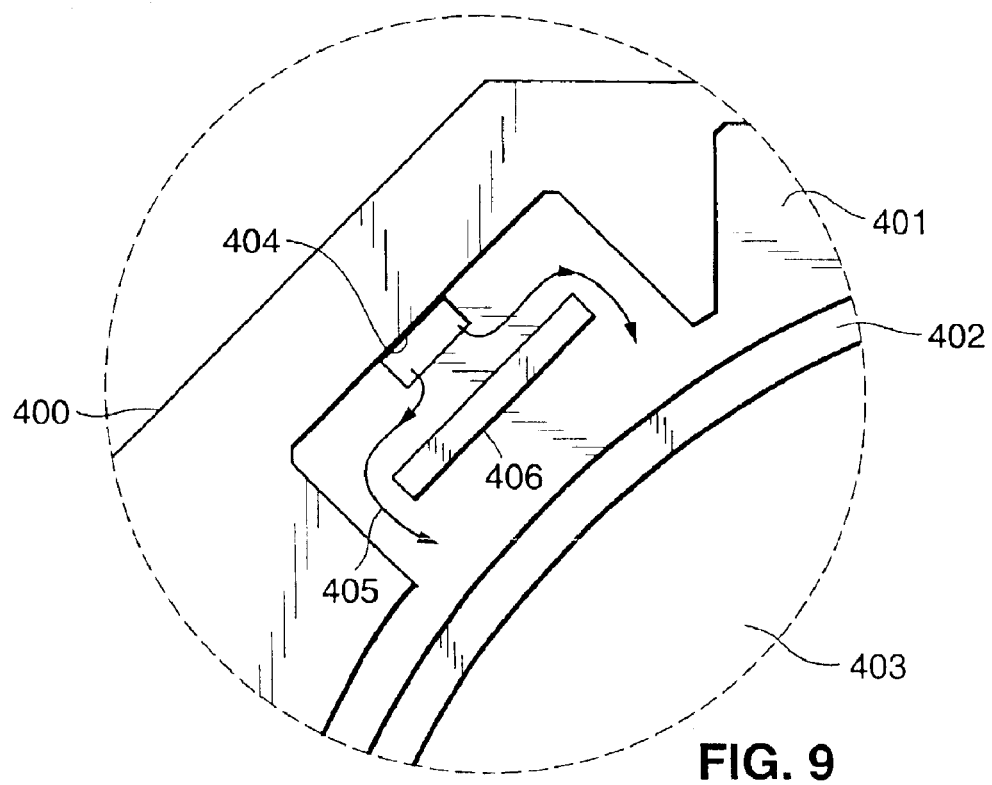
FIG. 9 illustrates one embodiment of a bubble-diversion element in a top-view.
Figure 10:
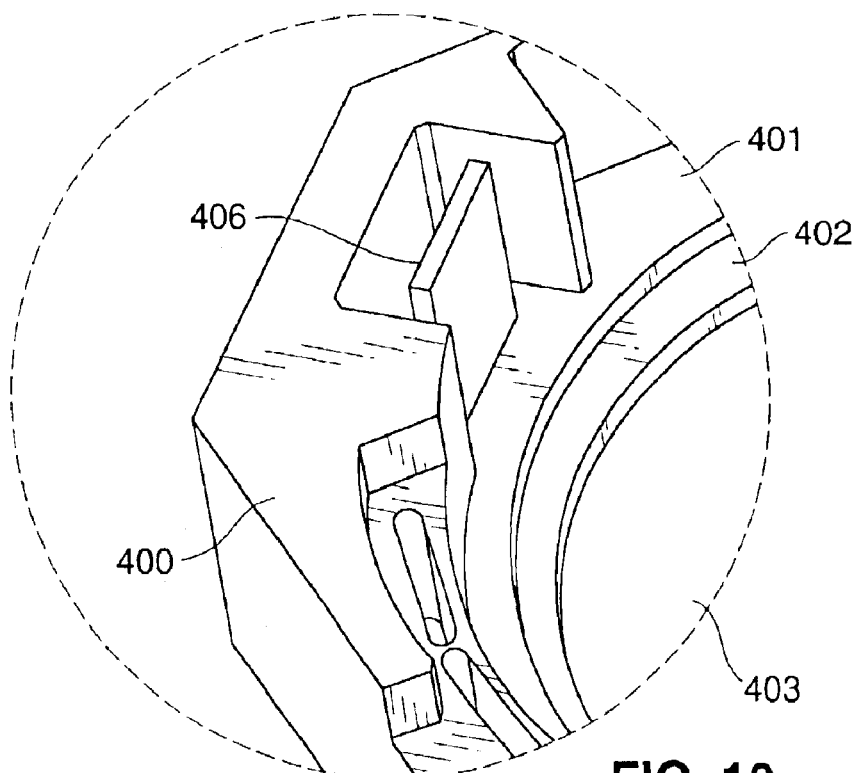
FIG. 10 illustrates one embodiment of a bubble-diversion element in a perspective-view.

When a wafer is measured while immersed, it is preferable to circulate water to avoid the build up of contaminants in the water, and to replenish water that is lost by evaporation, splashing, and wetting of wafers. FIG. 9 shows a cut away top view of a section of the water tank with wall 400 and floor 401 which has a lip 402 to support the window 403. Water is introduced at inlet 404, which is preferably lower than the minimum normal water level to reduce the possibility of creating bubbles. The incoming water 405 can carry with it bubbles that might adhere to either the window 403 or wafer (not shown) and impede the intended measurement of the apparatus. Bubble deflector 406 is desired to reduce the incidence of bubbles in the measurement region. It extends from the floor of the tank to a level above that of the water inlet and the water in the tank, as indicated in the three dimensional view of FIG. 10. Bubble deflectors in alternate embodiments may rely on increased residence times or vortical fluid motions.

Figure 11:
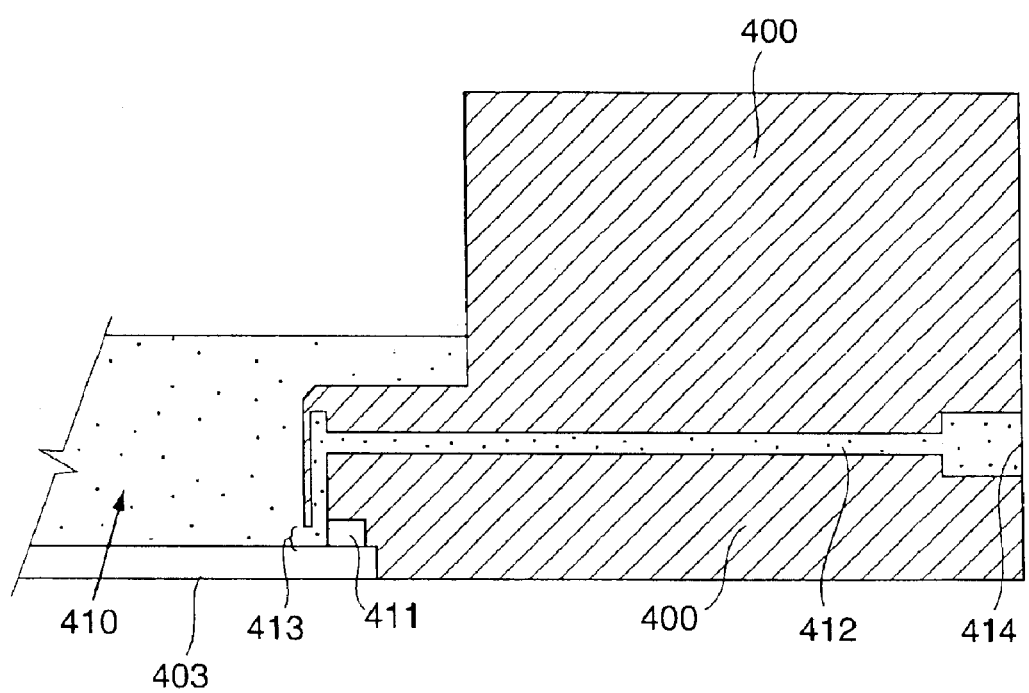
FIG. 11 illustrates one embodiment of a bubble-diversion element in cross-section.

It is also preferred to periodically clean the window. Slurry particles are the most likely source of contamination in the present context, although air-borne contaminants are also possible. Draining the water above the window facilitates cleaning. A preferred embodiment of a drain for this purpose is shown in the cut-away view of FIG. 11. The tank wall 400 and the window 403 contain water 410. An O-ring in grove 411 seals the window to the wall. Drain channel 412 has inlet 413 and outlet 414 where a fitting is attached. One or more such drains are preferably deployed around the perimeter of the window. These can be either interconnected and then connected to a vacuum source through a valve, or directly connected through valves to a vacuum source. The valve(s) is closed during normal operation of the system, and opened, to drain the tank. Typically, a water trap(s) will be placed in the line to capture the water and not pass it on to the actual vacuum source. In some cases, the very act of draining the tank will serve to remove contaminants.

Referring now to the embodiment of FIG. 1 and in alternate embodiments, optics breadboards 195, 197 may be positioned with a direct drive motor/lead screw. In a preferred embodiment, components of a motor are mounted directly on a lead screw shaft according to well-understood mechanical techniques. With a direct drive motor/lead screw, coupling elements are eliminated resulting in a more compact drive mechanism with high stiffness in torsion that enables precision positioning of the breadboards relative to wafer 110.

The wavelength range for illumination and collection may be in the ultraviolet (UV) or the visible or the near infrared (NIR) in different embodiments. In the particular embodiment in FIG. 1, reflectometer assembly 100 comprises a broadband reflectometer measurement system. Other embodiments may be narrowband or may comprise instruments other than a reflectometer. In FIG. 1, an illuminating light source (not shown) may be a UV Xenon lamp, fiber-coupled to the system shown in FIG. 1 via source fiber 103. Alternate embodiments have a tungsten lamp or a deuterium lamp or a xenon lamp. Relay optics 135 transfer collimated light from lens assembly 130 to beam splitter 104. The light transmitted directly through the beam splitter from the source fiber is referred to as the monitor beam. The monitor beam does not interact with measurement region 111. The portion of the illumination that the beam splitter directs toward the wafer is referred to as the measurement beam. The measurement beam reflects from the surface of the wafer, where its spectrum is modified by the presence of thin films on the wafer.

Following reflection from the wafer, the measurement beam returns to the beam splitter, and passes to several relay mirrors 135. First imaging optical assembly 137 focuses the measurement beam onto pinhole mirror 146. The light failing on a pinhole aperture in the pinhole mirror passes into spectrograph fiber 145, which conveys it to spectrograph 140. The resulting spectrum is a primary source of information about the films on the wafer. Other embodiments may image a portion of the wafer surface onto a spectrograph slit, thereby collecting data along a line on the wafer surface rather than a point.

Referring again to FIG. 1, the monitor beam follows a similar but distinct path through another pinhole mirror 146 and spectrograph fiber 145 to spectrograph 141. The measured monitor spectrum is indicative of the illumination and optical components, and may be used to correct the measurement of film properties for instrument characteristics.

As described above, the relative spectral content of both the incident and reflected light from semiconductor wafer 110 is measured. The thickness of thin-films deposited on the measurement region 110 can then be determined from the reflected measurement beam and incident monitor beam light by principles well known in the art. Many data reduction methods are applicable.

The embodiment illustrated in FIG. 1 has several advantages. First, as described above, an entire wafer surface can be quickly accessed. In addition, scanning with relay mirrors is employed in only one spatial dimension. If the light beams reflected from the relay mirrors were perfectly collimated and aligned, scanning would have no deleterious effects on the performance of the system. However, the beams cannot be perfectly collimated and perfect alignment is unattainable in practice. Therefore, it would be preferable to scan the objective with respect to the rest of the optics as little as possible. In the embodiment shown in FIG. 1, the majority of the optics scan in one dimension on the first optics breadboard, and the rest of the optics scan in two dimensions with respect to a laboratory-fixed coordinate system, but only one dimension (X) with respect to the first optics breadboard. Thus, the relay scan length is no more than one wafer diameter. In related art devices, the optics are fixed, and the objective scans in two dimensions, requiring a scan length of up to two wafer diameters.

A further advantage of the embodiments shown in FIG. 1 is that the optical path length remains constant, regardless of scan position. Thus, if the object is treated as a focal point, with a specular reflection from the surface of the wafer, the amount of beam spreading does not change. In related art devices, spatial scanning over a wafer surface changes the total optical path length, and thus the amount of beam spreading suffered by a collimated beam.

According to an aspect of this invention, locating a particular region of a wafer for measurement is achieved by imaging at least one field-of-view of a surface of the wafer. In the embodiment shown in FIG. 1, reflectometer assembly 100 measures selected regions of semiconductor wafer 110 as located and identified by imaging cameras. Large field-of-view camera 150 and small field-of-view camera 160 image the wafer surface with an approximately 20 mm×27 mm and an approximately 1 mm×1.3 mm field-of-view, respectively. In FIG. 1, a portion of the measurement beam reflected by pinhole mirror 146 is refocused onto small field-of-view (SFOV) camera 160. The resulting image is indicative of patterns on semiconductor wafer 110. The pinhole itself is also imaged onto the SFOV as a dark spot superimposed on the image of the wafer's patterns. This dark spot indicates the precise location where the reflectometer measurement is made with respect to the patterns on the wafer. Alternate embodiments may include a Fresnel lens and a beamsplitter plate or utilize dark-field illumination.

Figure 7:
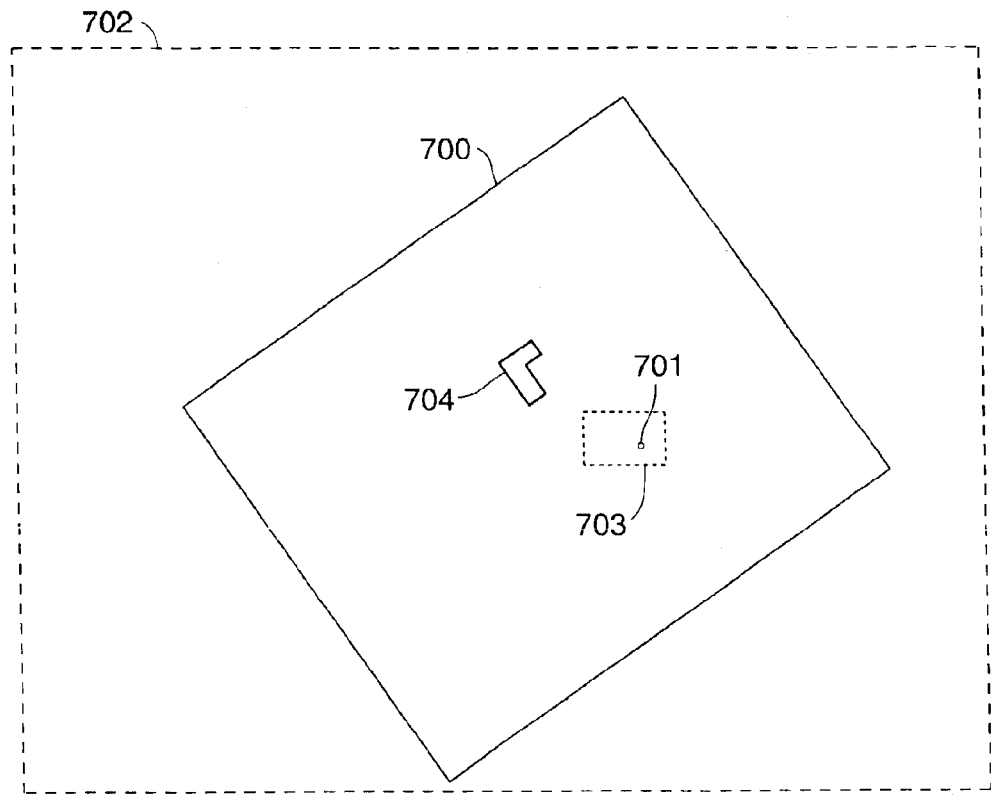
FIG. 7 illustrates the use of a large Field-Of-View (LFOV) camera and a small Field-Of-View (SFOV) camera to avoid groping in the process of locating a particular region of a wafer.

FIG. 7 illustrates the use of a large Field-Of-View (LFOV) camera and a small Field-Of-View (SFOV) camera to image a wafer surface and avoid groping in the process of locating a particular region of a wafer. In FIG. 7, die 700, LFOV 702, SFOV 703, LFOV pattern 704, and SFOV pattern 701 are shown.

LFOV 702 is generally larger than die 700, and much larger than the uncertainty in the location of the center of the wafer. Thus, it can be moved to a location where it will certainly find LFOV pattern 704 on a die of a randomly oriented wafer. Once the LFOV pattern has been found, the system has much better knowledge of both the orientation of the wafer and the location of its center. Thus it is able to position the SFOV 703 over the SFOV pattern 701 without groping. This process has a deterministic time that is much shorter than the worst-case scenario for groping with just a SFOV, or than the time for physically aligning the wafer.

Figure 8:
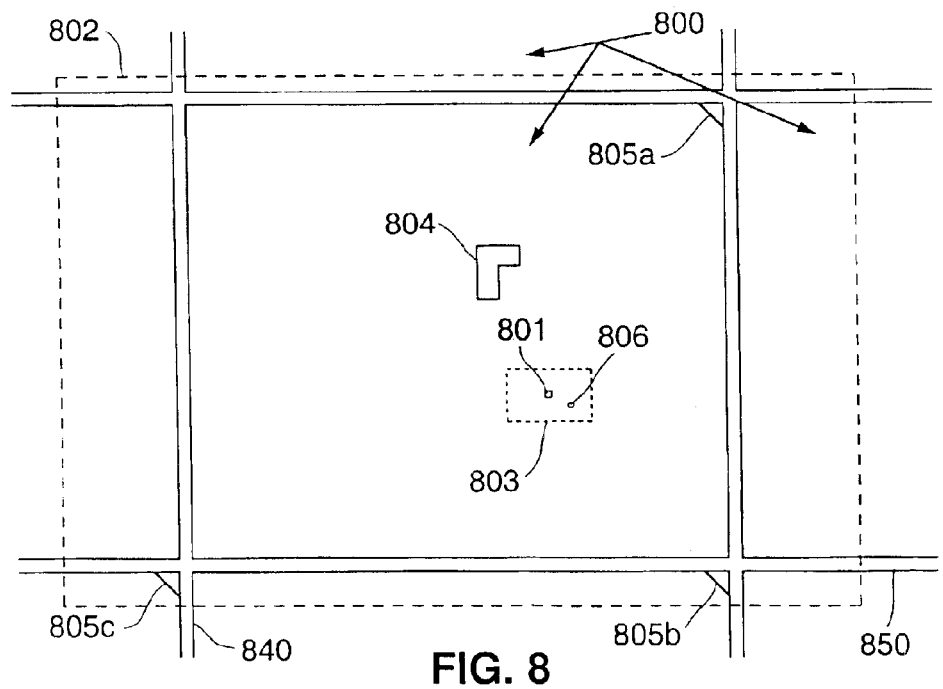
FIG. 8 illustrates the advantage of using of the LFOV camera to enable easy die size determination during training.

FIG. 8 illustrates the advantage of using of the LFOV camera to enable easy die size determination during training. In FIG. 8, dies 800, inter-die streets 840, inter-die alleys 850, die features 805a–c, large field of view 802, small field of view patterns 803, 804 and 801, and measurement site 806 are shown.

For training purposes, operators find it advantageous to view the wafer right side up, and moreover to orient the wafer so that inter-die streets 840 and alleys 850 appear vertical and horizontal, as shown in FIG. 8. However, such an orientation of the wafer is not necessary and other orientations are possible in alternative embodiments. An initial rough estimate of die size can be made from three occurrences of a die feature, e.g. 805a–c, selected by the operator on three different dies. The system can then use pattern recognition and the LFOV and/or SFOV cameras to obtain a very accurate determination of die size by locating LFOV and/or SFOV patterns, 804 and/or 801, on various dies on the wafer. With this method, it is not necessary for the operator to know the die size a priori.

Another advantage of the LFOV camera is ease of training human operators to correlate measurement sites and patterns in the SFOV with the position on the wafer. Ideally, the large field of view covers a whole die, as shown in FIG. 8. Using large field-of-view 802, an operator can select the region of the die 800 to view with SFOV 103. This is similar to using a state map to navigate to a particular city. Once the SFOV has been properly positioned, the operator can very precisely select SFOV pattern 801 and the measurement site 806. This is similar to finding the correct intersection on a city map.

In a preferred embodiment, there may be a multiplicity of measurement sites within a die. In such cases, different sites may have different 'stacks' of layers that are to be measured. The thickness algorithm, i.e., the parametric minimization of a cost function as discussed in U.S. Provisional Application Ser. No. 60/125,462, generally needs to have a priori information, the algorithm recipe, about each stack that is measured. In cases where there are multiple sites per die with different stacks, the system must either use multiple algorithm recipes, or have a general algorithm recipe to accommodate the different stacks.

The reflectometer shown in FIG. 1 is included for purposes of illustration and not limitation. Alternate embodiments of the imaging metrology device comprise other metrology systems, including acoustic systems. Such alternate metrology system may be coupled to the same optics breadboards shown in FIG. 1 for reflectometer system 100. Particular embodiments may also require the use of flexural bearings for smooth repeatable motion on micrometer or sub-micrometer scales.

Exemplary alternative embodiments include a profilometer to determine amounts of recess, dishing, or other departures from planarity of a wafer surface and a profilometer in combination with a reflectometer. In different embodiments, a profilometer may be an acoustic profilometer or an optical profilometer. A particular embodiment of an optical profilometer may use the auto-focus system described in U.S. Provisional Application Ser. No. 60/125,462, to determine a relative profile of a wafer surface. The auto-focus system is inherently sensitive to the profile of the wafer surface since departures from planarity of the wafer surface will cause differences in the focusing of light rays reflected from the wafer surface.

Other embodiments of this wafer metrology device may include an ellipsometer or high-contrast imaging microscopes. Particular embodiments may utilize aspects of differential interference contrast (DIC) techniques. Polarization techniques may be incorporated to infer quantitative information about the wafer surface according to techniques well known in the art. In particular embodiments, an integrated interferometer, and imaging spectrograph may be used to simultaneously determine the wafer surface's profile and material content. Preferred embodiments further comprise motion control systems, image pattern recognition systems, and software to determine the quantities of interest from measured data. These elements are well known in the art.

It is noteworthy that in the embodiment shown in FIG. 1, semiconductor wafer 110 is located above reflectometer assembly 100. In alternative embodiments, the semiconductor wafer may be held in a pool of water above or below the optical system. With the wafer below the optics, the system may be configured to 'look' down instead of up. This would necessitate differences from FIG. 1 in the handling of the wafer, which would have its IC device side up. In such alternate embodiments, either the optical system (including a main window) may be lowered toward the semiconductor wafer or the semiconductor wafer may be raised toward the optical system. Such an alternate embodiment would be a 180 degrees rotation of the system about a horizontal axis, as compared to FIG. 1. General rotations of the system relative to the configuration shown in FIG. 1 are also possible, e.g., 90 degrees. The main impact of such rotations is on the wafer handling techniques.

In particular alternative embodiments of the invention, there may be no water in the measurement path. That is, the instrument is 'dry'. In such embodiments, the orientation of the instrument relative to the laboratory may be arbitrary. For example, the embodiment of FIG. 1 could be operated on its side or upside down. While redesign of some of optical components might be preferred in such cases, it would not be necessary.

As can be appreciated by the skilled person, many other optical layouts than that shown in FIG. 1 are also possible without departing from the invention, including embodiments using substantially all reflective optics including curved reflectors. As one skilled in the art will recognize, the use of reflective optics has several advantages including minimizing Fresnel reflections, and chromatic bandwidth limitation and aberrations. In certain embodiments, however, refractive optical components are preferred since reflective optics may introduce constraints on aperture and geometry. In such embodiments, the optical system is color-corrected and if the semiconductor wafer is immersed in water, the water is considered as an optical component.

Figure 12:
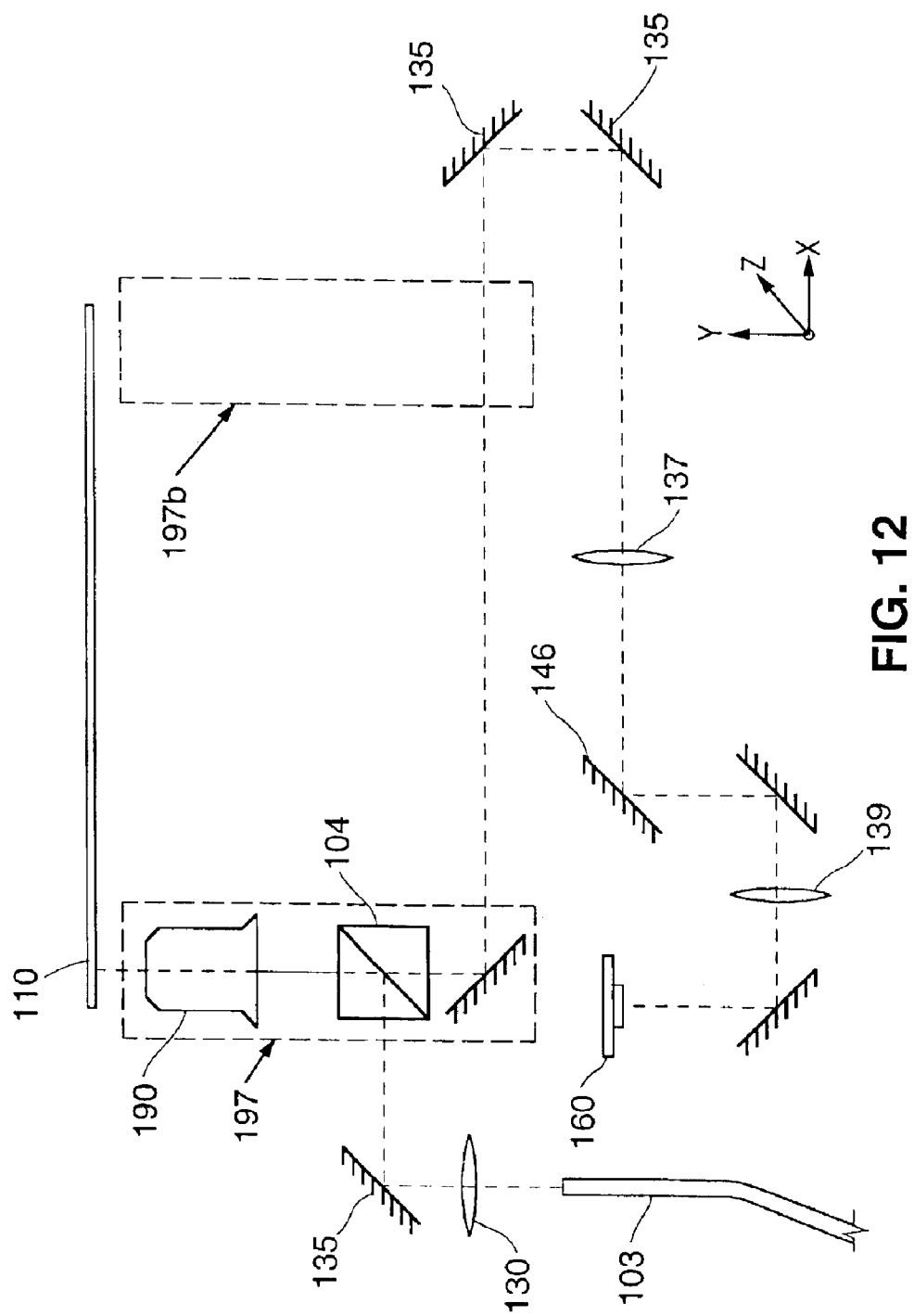
FIG. 12 shows one embodiment of an illumination system.

An embodiment of an illumination system illustrated in FIG. 12. The illumination system must fill the desired (small) field of view of objective 190, to allow for pattern recognition. It must fill the desired numerical aperture of the system to achieve a small (diffraction) spot size. It must maintain uniform light level, especially at the center of the field of view, where the pinhole mirror 146 samples light for spectral measurement, especially as the second optics breadboard 197 translates in the X direction. The effective light source for the system is the end of the fiber 103. The objective 190 and imaging lens 137 form an infinite conjugate imaging system. This allows scanning of the second optical breadboard 197 in the X direction with negligible changes in magnification or focus. The objective collimates light emanating from points on the wafer, and the imaging lens focuses collimated light onto the pinhole mirror 146.

One embodiment is a system with "critical illumination", as shown in FIG. 12 where collimator 130 collimates light from the end of fiber 103 which is then imaged onto the field of view on wafer 120. The advantage of critical illumination is that illuminating light is collimated. When the second optics breadboard 197 moves in X, e.g., to 197b, the same bundle of rays from the same point on the end of the fiber is imaged onto the center of the field of view where the measurement spot lies. Thus the measurement intensity is not affected by X position if the system is properly aligned. A potential problem with critical illumination is that non-uniformities in the illumination at the end of the fiber may be superimposed on the image of the wafer as seen by the camera.

A standard illumination system used in related art is Kohler illumination. In true Kohler illumination, the light source is imaged onto the illumination pupil of the objective and the aperture associated with the light source is imaged onto the field (wafer). Any non-uniformity versus position on the fiber end is converted into non-uniformity versus incident angle on the wafer, which is generally not apparent. The intensity distribution versus angle at the fiber, which should be nearly uniform, is converted into uniform intensity versus position on the wafer. True Kohler illumination is not possible with the geometry shown in FIG. 12, since the illumination pupil of the objective moves relative to the fiber, so that the proper focus is not maintained.

Figure 13:
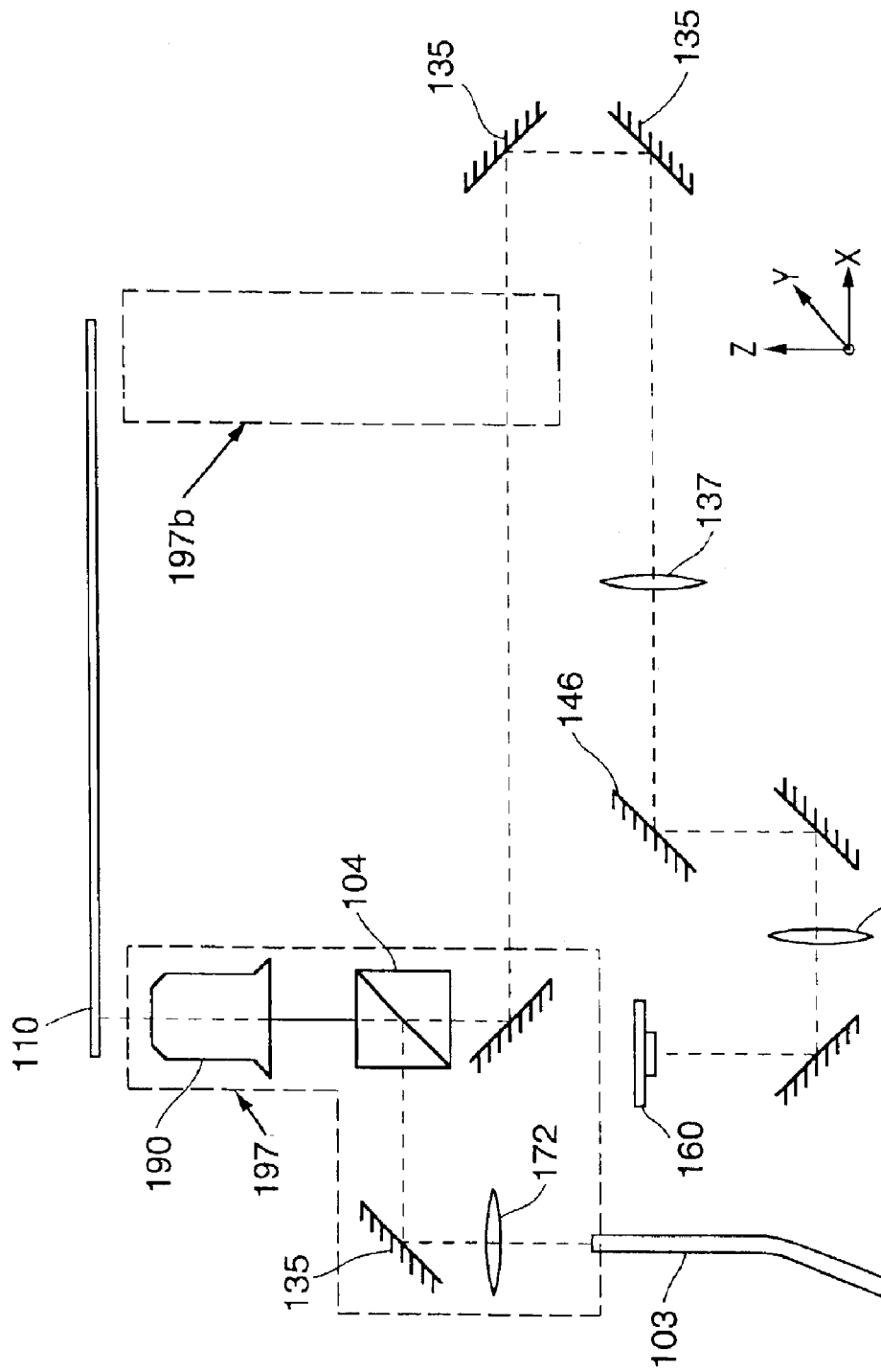
FIG. 13 shows an alternate embodiment of an illumination system.

FIG. 13 illustrates an embodiment with Kohler illumination. The embodiment in FIG. 13 allows Kohler illumination by fixing the fiber and illumination optics to the second optics breadboard, so that they move together. In this case, Kohler optics 172 in FIG. 13 replace collimator 130 in FIG. 12, and the fiber 103 flexes for motion of the second optics breadboard in both X and Y.

Figure 14:
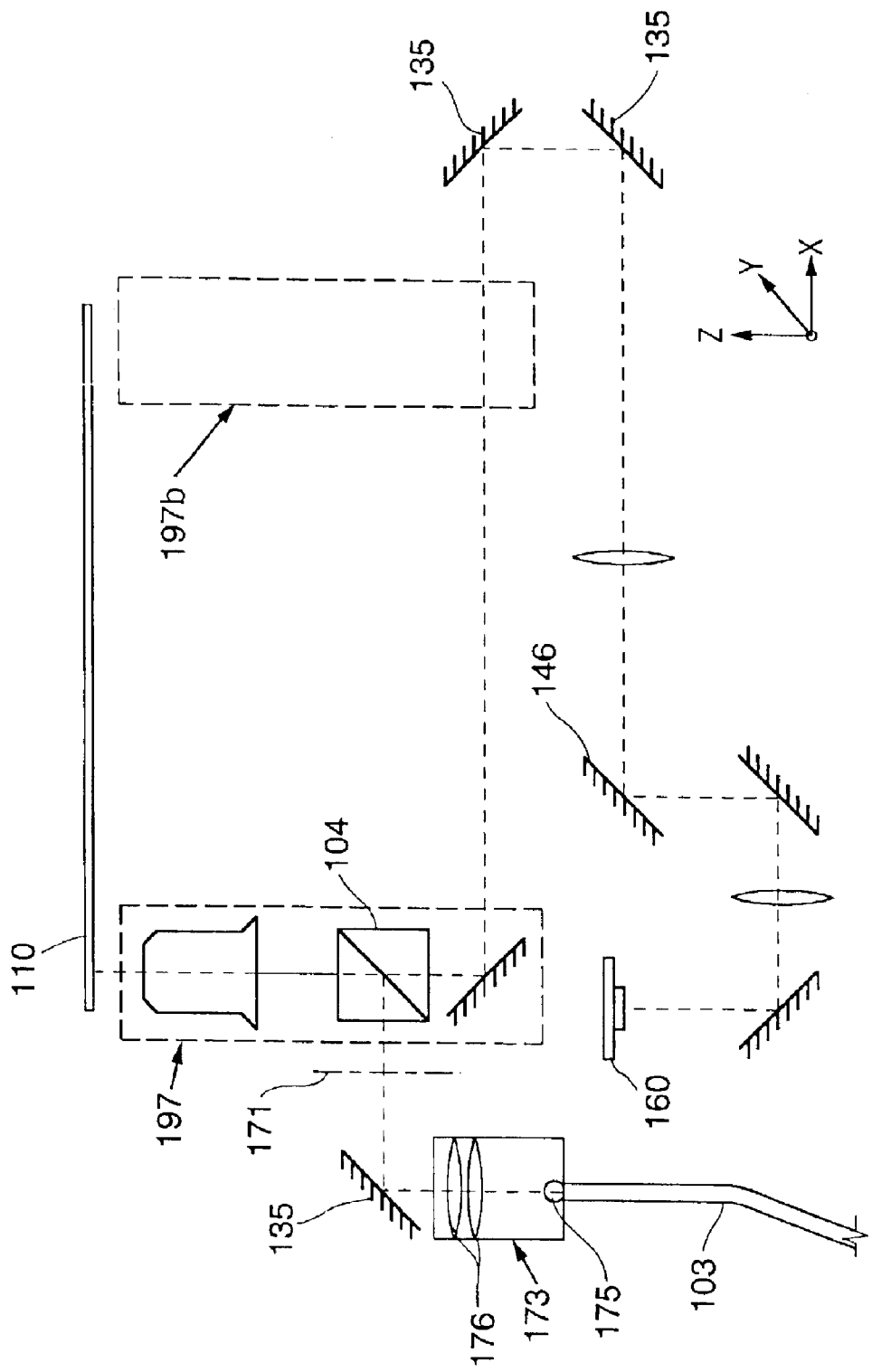
FIG. 14 shows a second alternate embodiment of an illumination system.

A preferred embodiment of the illumination for the small field of view is pseudo-Kohler, as shown in FIG. 14. The pseudo-Kohler optics 173 image the end of the fiber 103 at a plane 171 just in front of beamsplitter 104 when the second optics breadboard is in its position closest to the illumination optics. To enlarge the image of the fiber to the size of the objective aperture in a short length requires the illumination optics to have a short focal length. Most of the magnification in the illumination optics is done by sapphire ball lens 175. The exit aperture of the fiber, which initially is at infinity, is imaged by the ball to a plane near the second surface (top) of the ball. The two plano-convex lenses 176 image the aperture at a point nearly at infinity, and objective images fiber aperture close to the wafer.

Figure 15:
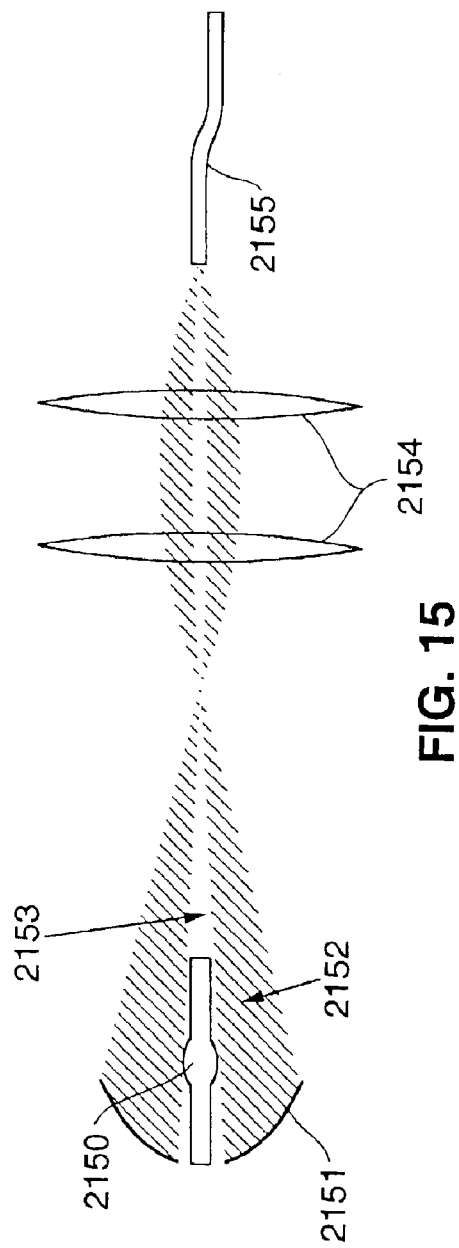
FIG. 15 shows an embodiment of lamp-fiber coupling.

FIG. 15 shows the illuminator hardware of an embodiment of the invention. The illuminator supplies light to the illumination fiber 2155. Xenon arc lamp 2150 emits light that is focused by perforated elliptical mirror 2151 to produce illuminating rays 2152. The perforation of the mirror and the presence of the arc lamp produce a shadow zone 2153. The relay lenses 2154 project illuminating rays and shadow zone onto the fiber tip. The shadow covers a range of angles, as opposed to position. This angular shadow tends to propagate through the fiber and out the other end. This angular shadow may be converted by Kohler and pseudo-Kohler illumination to a shadow positioned in the center of the illuminated field.

Figure 16:
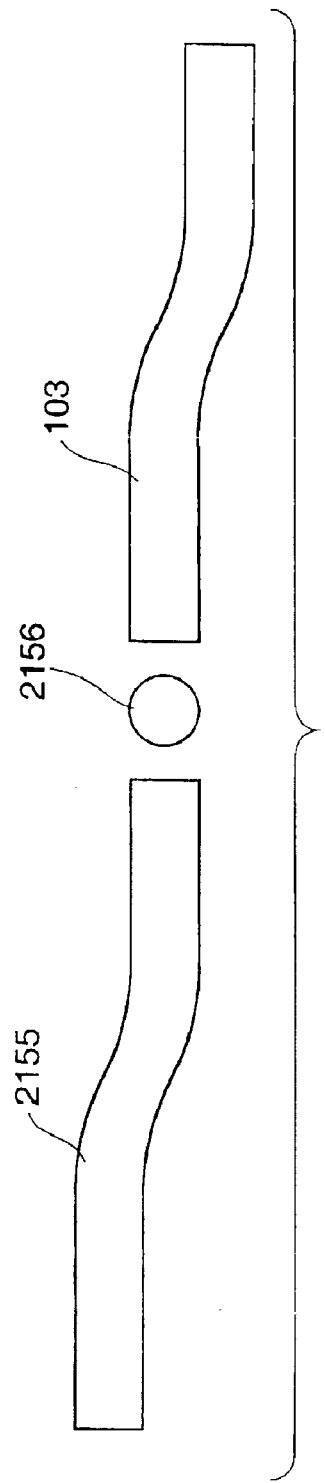
FIG. 16 illustrates an illumination embodiment with fiber-to-fiber coupling.

FIG. 16 shows an embodiment that solves the problem of the angular shadow discussed above. In this embodiment, a ball lens 2156 is inserted between fiber 2155 coming from the illumination system and fiber 103 that goes to the instrument. The ball lens images the exit pupil of the fiber 2155 onto the (input) surface of fiber 103, and the exit surface of fiber 2155 onto the entrance pupil of fiber 103. Thus roles of position and angle on the two surfaces are interchanged. The light leaving fiber 2155 is relatively uniform as a function of position but suffers from the shadow 2153 as a function of angle. The light entering fiber 103, after passing through the ball lens is uniform in angle, and now shadow 2155 appears in the spatial pattern of illumination. Due to the effect of fibers to spatially homogenize the illumination pattern, the light leaving fiber 103 will tend to be uniform in both angle and position, and a suitable source for Kohler or pseudo-Kohler illumination, or even for critical illumination, if the end of the fiber is very uniform. Alternate embodiments including light collectors, or condensers, or funnels are also possible.

Figure 17:
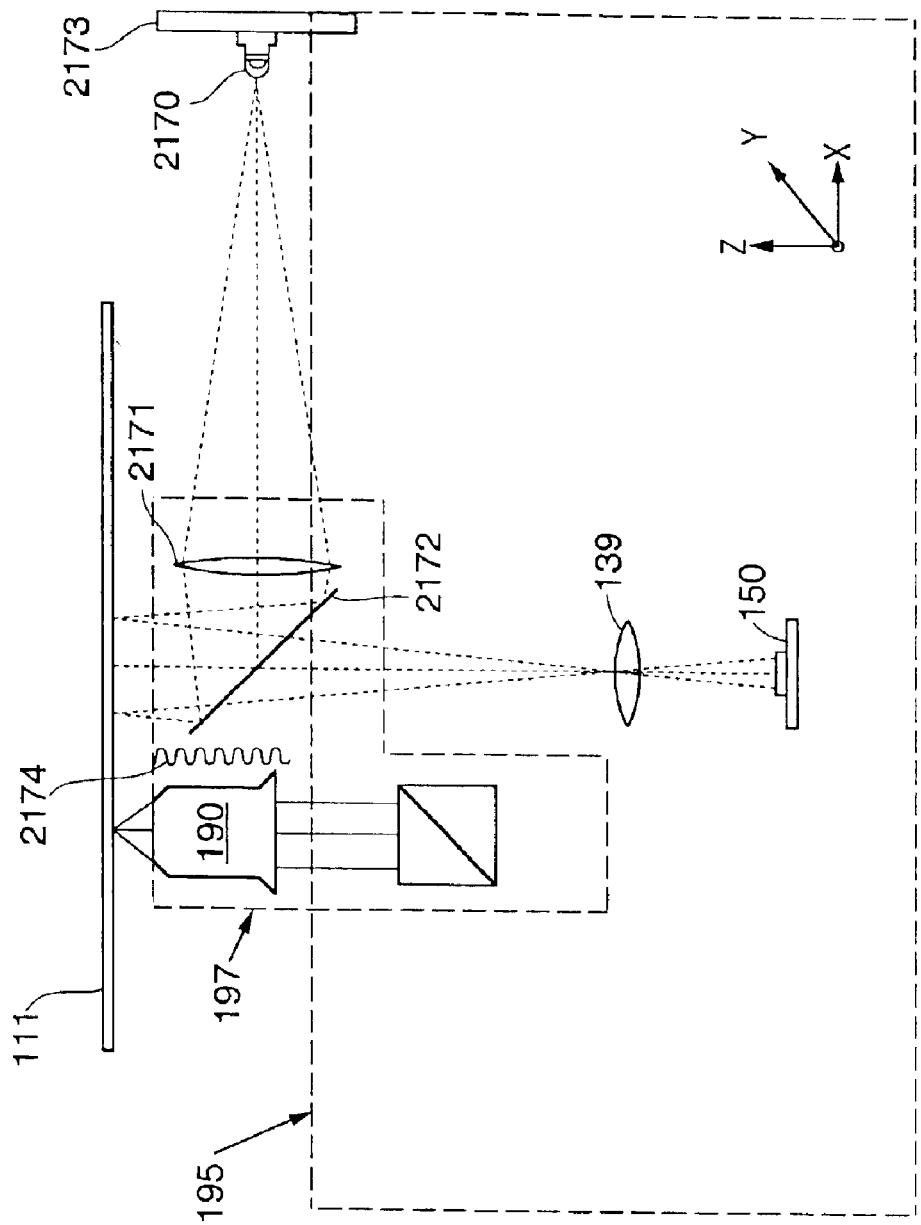
FIG. 17 shows a preferred embodiment for illumination of a LFOV camera.

A preferred embodiment for the illumination of the large field of view (LFOV) is shown in FIG. 17. The light source 2170 is preferably a LED. First optical breadboard 195 holds the light source 2170 on support 2173, which allows for alignment of the light source with the rest of the illumination system to be described. The whole LFOV optical system thus translates in Y with the first optics breadboard 195. The second optics breadboard 197 holds the other two components of the LFOV illumination system, lens 2171 and beamsplitter 2172. Light from the source 2170 passes through the lens, reflects from the beam splitter and illuminates the wafer 111, where it is reflected and passes through the beamsplitter 2172 on its way to the LFOV lens 139 and ultimately the LFOV camera 150. In order to produce Kohler illumination, illumination lens 2171 preferably focuses the light into the entrance pupil of imaging lens 139. Focusing lens 2171 is preferably a Fresnel lens, binary optic, or some other diffractive optic, to reduce its physical thickness so that it restricts the movement of second optical breadboard 197 as little as possible. Beamsplitter 2172 is preferably a plate-type beamsplitter. Preferably optical absorber/diffuser 2174 prevents light which passes horizontally through the beamsplitter from reflecting off other surfaces (e.g., objective 190) and being reflected by the beamsplitter down towards the camera. The LED and dimensions are chosen so that the light uniformly illuminates the desired LFOV on the wafer.

Both the large and small field-of-view imaging systems preferably include filters to enhance contrast for various types of wafers. In embodiments with the simplest implementation, these are filters yield good contrast over a wide range of wafers, and are built into the system. Preferably, the filters can be selected, possibly under computer control, to allow for better contrast on a wider range of wafers. The SFOV optical train includes the pinhole mirror, which samples light for the spectroscopy measurement. It is advantageous to have the filter after the pinhole mirror, so that it does not restrict the spectral range of the measurement not reduce the amount of light entering the spectrometer. In embodiments where the filter is before the pinhole mirror, it should be movable; to allow images for pattern recognition to be recorded with the filter, and spectra to be acquired without the filter. A preferred means of moving the filter, in this case, is a computer-controlled flipper mechanism. To save space inside the instrument, the moveable filters may be placed before the fiber in the collimated space of the illumination optics.

Filters are preferred in embodiments where the light source is broadband, e.g., white, as discussed above. In some embodiments, the illumination is narrow band, e.g., an LED or laser. In these embodiments, it is advantageous to have selectable colors, so that selecting the best of the emitted wavelength bands can enhance the image contrast. One embodiment with selectable colors is with multiple devices having different colors. These can be selected by either mechanically moving them into position, or with beamsplitters. A preferred embodiment uses a two color LED, which allows purely electronic selection without impacting footprint or illumination alignment.

According to this invention, the cameras for the two fields of view can operate in a number of different modes, with tradeoffs in throughput, and signal to noise ratio. The cameras can have fixed, computer selected or camera-selected shutter speed. The cameras can have fixed, computer selected or camera-selected gain. It is desirable to have selectable shutter speed and gain, in order to get good image signal to noise ratio on a wide variety of wafers. In camera selected mode, electronics associated with the cameras examine the intensities at the pixels and choose 'good' values to balance saturation at some pixels and low levels at other pixels. An alternative to camera selection is computer selection, where the instrument's computer commands shutter-speed and gain. The basis for the commands is from analyzing images either at run time, to yield the best signal-to-noise ratio, or at training time, to maximize run-time throughput. A hybrid approach of particular embodiments allows the camera to adjust the value(s) at training time when the computer reads the values, and the computer sets the values at run time.

In a preferred embodiment, a window separates the wet wafer from the dry optical system. This mirror is preferably anti-reflection coated to reduce reflections at its surface. It is more important to coat the dry side of the window than the wet side, since the reflections at air/glass interfaces are greater than those at water/glass interfaces.

Making fast and accurate measurements of film thickness is an object of the invention. To some extent, the algorithm used to reduce spectral data to infer film thickness(es) can trade speed for accuracy: a more accurate algorithm takes more time. The algorithm may be one of the most CPU intensive tasks for the instrument's computer. According to the principles of this invention, the tradeoff between time and speed may be overcome by using asynchronous data processing. Synchronous data processing means that each spectrum is processed after it has been acquired and before the instrument does anything else. Asynchronous data processing means that after a spectrum is acquired, the computer commands the instrument to proceed with data collection, and processes the acquired spectra while it is waiting for the rest of the instrument to execute commands, e.g., stage motions. In preferred embodiments, this may be implemented with multi-threaded programming. In such embodiments, threads of relatively low priority process backlogged data, while other threads of higher priority continue data collection as fast as the instrument will allow. Multiple spectra may be backlogged. For an algorithm of a particular embodiment, asynchronous data processing is at least as fast as synchronous processing, and may be significantly faster. In a preferred embodiment, data from previously measured wafers is not allowed to accumulate, i.e., all the data from one wafer is processed before data from the next wafer is acquired.

Figure 4A:
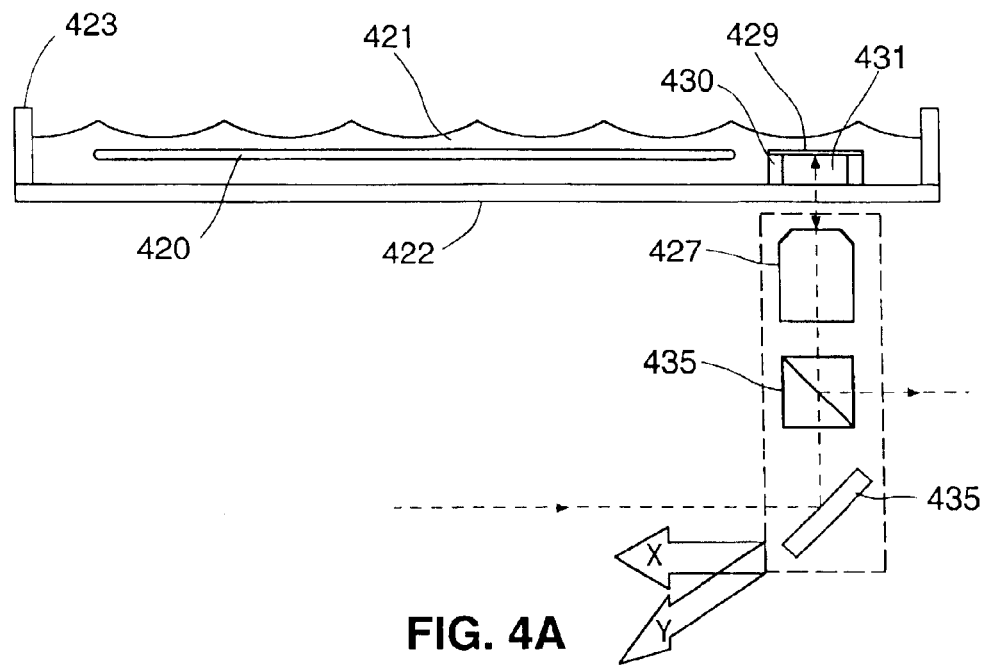
FIG. 4a shows an exemplary reference reflector embodiment.

To achieve accurate measurement results with a data reduction method, preferred embodiments use a reference reflector to collect data allowing a correction for slowly varying characteristics of the measurement system in a data reduction method. FIG. 4a shows an exemplary embodiment with a reference reflector. In FIG. 4a, wafer 420, window 422, reference reflector 429, reference volume walls 430, reference volume 431, main volume of water 421, objective lens assembly 427 and relay optics 435 are shown.

In FIG. 4a, reference volume walls 430 separate the reference volume 431 from the main volume of water 421. Reference volume 431 may be filled with air, water, or other suitable substances. It is preferred that the reflectivity of reference reflector 429 is very stable over time. The distance between window 422 and the reference reflector can be adjusted if volume 431 is not filled with water, to put the reflector in focus when the objective lens assembly 427 is the same distance below the window 422, as when the wafer is in focus. In a preferred embodiment, the volume is filled with an inert solid, and the height of the reflective surface above the window 422 is adjusted appropriately.

Reference reflector 429 may be of silicon, fused silica, chromium or any other inert material. It may comprise layers of deposited material on a substrate to achieve mechanical and optical stability. In a preferred embodiment, the reference reflector comprises a fused silica substrate with a chromium film on a top surface. An alternative embodiment of the reference reflector uses silicon with a reflective oxide layer on a lower surface.

Referring to FIG. 4a, reference reflector 429, reference volume walls 430 and the window 422 may be assembled in differing ways. In a preferred embodiment, the reflector and window are hermetically sealed to the window. In an alternative embodiment, the reference reflector, reference volume walls and the window are held together with a polymer adhesive, e.g., epoxy or super glue. In other embodiments, volume 429 is not sealed off from main volume 421. The components are either bonded together or held in place mechanically, for example with stops and springs. The reference volume is sealed in order to preserve the reflectance of the reflector, i.e., to avoid it getting dirty or corroded due to materials introduced into the bath, e.g., CMP slurry. Sealing volume 431 avoids the problem of breaks or leaks caused by different thermal expansion coefficients, either during operation or shipping.

In preferred embodiments, reference reflector 429 is placed in a position where the objective lens assembly 427 can have direct access to it. Preferably, the objective lens assembly can scan in at least one dimension, and move to the location of the reference reflector. However, in embodiments where the wafer scans over the objective, the reference reflector may do so as well. While a preferred embodiment has the wafer above the objective lens assembly as illustrated in FIG. 4a, alternate embodiments may have the objective lens assembly above the wafer, or at an arbitrary inclination.

According to aspects of this wafer metrology device described above, a reference spectrum from the reference reflector 429 is collected periodically. Following collection of a reference spectrum a data reduction algorithm utilizing the reference spectrum is used to calculate film thickness from spectra collected from wafer 420. Preferably, a reference spectrum is collected every time just prior to a wafer measurement. There are numerous ways to include the reference spectrum from the reference reflector into a data-reduction algorithm. In one embodiment, every spectrum from the wafer is normalized with the most recently measured reference spectrum from the reference reflector.

Calibration of the measurement apparatus may utilize a calibration wafer and the spectrum collected from it. Calibration adjusts the algorithm described above so that it gives the correct answer for the calibration wafer. The reference spectrum should be used by the algorithm at calibration in the same way that it is used during measurements of wafers, so that any changes in the system between the last calibration and the current measurement will not affect the results of the algorithm.

As described, embodiments of this wafer metrology device (see FIG. 1 and FIG. 4a) may include a reference reflector and dual spectrographs. The primary data for the measurement is the spectrum S, which is the system's output representing reflection from the sample under test. In addition to the properties of the sample, S depends on the characteristics of the broadband (UV, visible, NIR) illumination, the optical system, detectors and digitizers and other elements that comprise a measurement system. Such measurement system characteristics obscure information about the sample. Thus, an accurate measurement of film thickness should remove their effects.

In FIG. 1 the sample under test is the semiconductor wafer 110. It is noteworthy that the sample may also be the reference reflector or the calibration reflector, as discussed above. From FIG. 1, the optical path for light determining the monitor spectrum may be similar to the optical path for the light determining the measurement spectrum, except for transit to and from measurement region 111. A preferred embodiment of the two beams is shown in FIG. 1. In preferred embodiments, the illumination source may be identical for both beams.

Figure 4B:
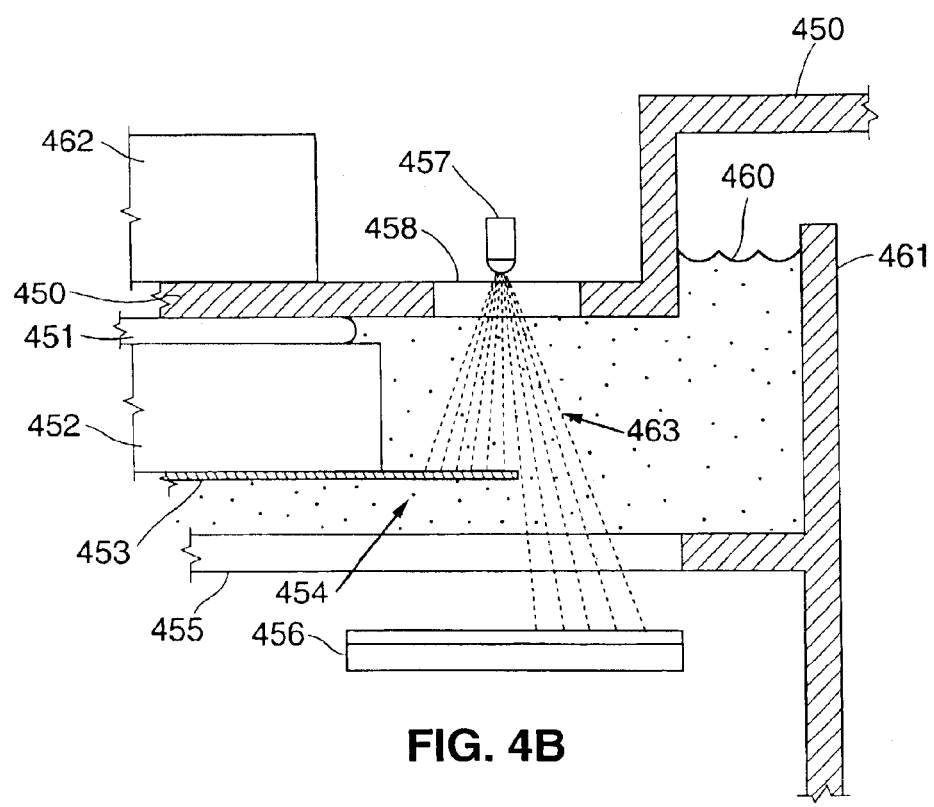
FIG. 4b shows an exemplary embodiment of the wafer aligner.

FIG. 4b shows an exemplary embodiment of the alignment system allowing rapid alignment of a wafer with the optical system. In FIG. 4b, wafer 453, rotary chuck 452, motor 462, water 454, window 455, water level 460, motor housing 450, rotary seal 451, light source 457, light 463, alignment window 458, detector 456, and tank wall 461 are shown.

In FIG. 4b, rigid rotary chuck 452 holds wafer 453. Motor 462 turns the rigid rotary chuck about an axis (not shown). Water 454 fills the area above main window 455 up to water level 460 and over to tank wall 461. Rotary seal 451 seals motor housing 450 from the water. Light source 457 is also in a dry housing. The light source produces light 463 that passes through alignment window 458 from the dry housing into the water. Detector 456 is in the dry volume below window 455. Some of the light 463 strikes wafer 453 and is blocked. The rest of the light passes through main window 455 into the dry volume below it, and onto the detector.

Rigid rotary chuck 452 rotates wafer 453. As the wafer rotates, the edge of the wafer that is directly over the detector moves in a radial direction (to the left and right in FIG. 4b). The radial motion arises due to the wafer being off-center on the rigid rotary chuck or not being perfectly round. Aside from machining tolerances, the presence of a fiducial notch or flat on the rigid rotary chuck causes the wafer to be out of round.

Radial motion of the edge of wafer 453 over detector 456 changes the shadowing of light 463 which falls upon the detector. The detector can be either a single long detector, e.g., a photo-diode, or an array of detectors, e.g., a charge coupled device (CCD). In the former case, the total amount of the light falling on the detector is an indication of position of the edge of the wafer. As the edge of wafer 453 moves to the right in FIG. 4b, the amount of light falling upon the detector decreases. In general, the output of the detector, I, is some function of the position of the edge of the wafer, xe;

$$I=f(xe), \quad (1)$$

The quantity I is not necessarily linear but is monotonic, so that it's inverse $$xe=f^{-1}(I), \quad (2)$$

may be used to determine the location of the edge.

In an alternate embodiment, the detector may consist of an array of detectors, with each element in the array having a different location, $X_a$. In this case the intensity of light falling on the different detector elements gives rise to a waveform:

$$I(x_a)=g(x_e). \quad (3)$$

The quantity I can be processed by an algorithm, h, such that $$x_e=h(I(x_a)) \quad (4)$$

Functions g and f may be complicated, due to wave-optics considerations (FIG. 4 is illustrative only of ray-optics). Determination of f or g is by calibration.

Figure 5:
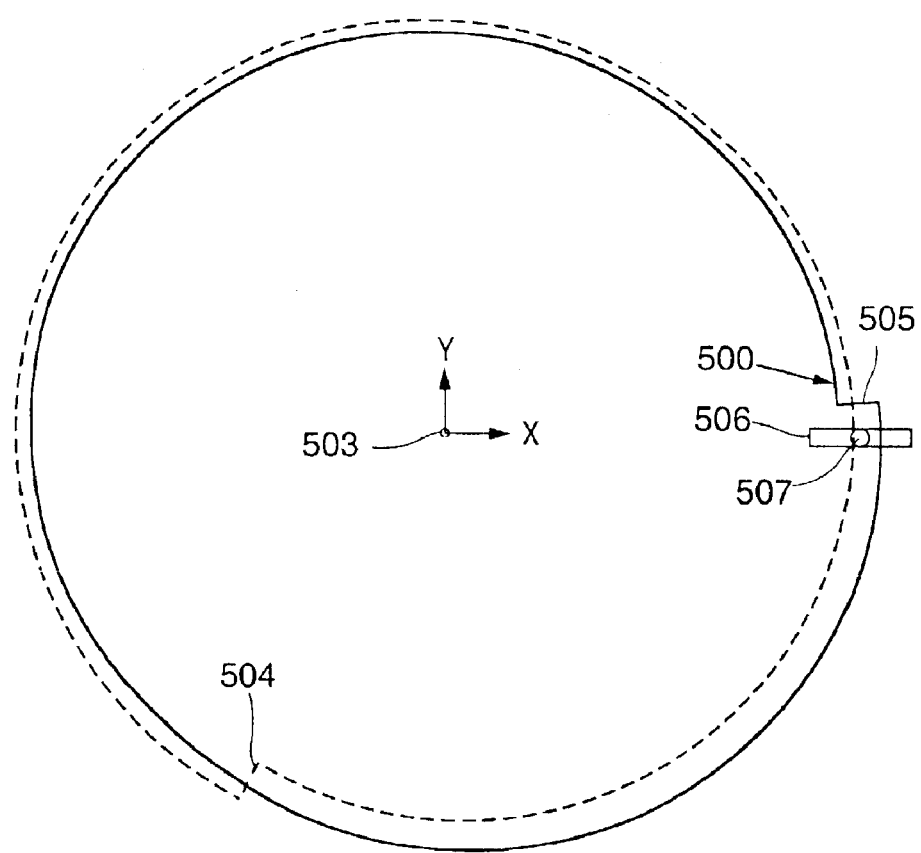
FIG. 5 illustrates calibration of the wafer aligner.

FIG. 5 illustrates calibration of the wafer alignment. In FIG. 5, spiral wafer 500, chuck 503, spiral edges 504 and 505, detector 506, and source 507 are shown.

Spiral wafer 500 has a thickness comparable to that of a silicon wafer; is made from a durable, clean, machinable, opaque material, e.g., stainless steel; and has a mechanical index to insure that its center is aligned with the center of the chuck 503. As the chuck rotates, the spiral edges 504 and 505 block amounts of light emanating from source 507 from reaching detector 506. As the spiral rotates, the system records the detector output as a function of angle. The discontinuity in the radius of the spiral 505 indicates when the spiral is over the detector. The radius of the spiral as a function of angular displacement from the discontinuity 505 is known. Thus, the functions $g(x_e)$ or $f(x_e)$ can be recorded, so that $f^{-1}$ or h can be calculated for use with real wafers.

The outcome of the above-described measurement enables the calculation of the location of a notch or flat on the wafer, and the location of the center of the wafer with respect to the center of the chuck, from 1 for a set of rotations covering 360 degrees with $f^{-1}$ or h.

Figure 6:
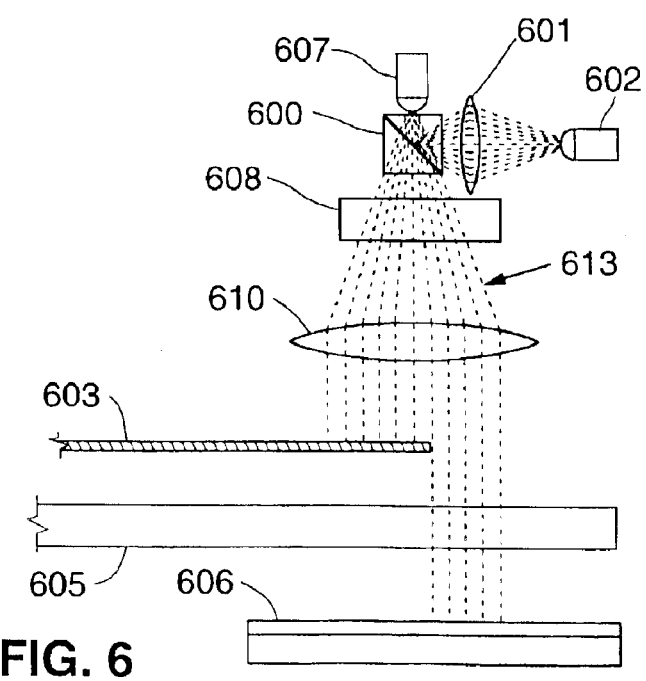
FIG. 6 illustrates improved accuracy of wafer alignment.

FIG. 6 shows another aspect of the wafer metrology device that improves the accuracy of wafer alignment. In FIG. 6, beam splitter 600, lens 601, reference detector 602, light source 607, window 608, rays 613, collimating lens 610, and wafer 606 are shown.

In general, the intensity of the source 607 can vary as a function of, e.g., time and temperature. In order to correct or compensate for this, some portion of the light can be deflected by a beam splitter 600, possibly focused by lens 601, and detected by reference detector 602. The output from the reference detector can be used either to control the output intensity of the source, or to correct the inversion of data for variations in the source.

FIG. 6 shows another exemplary illumination scheme. In this case the source 607 produces diverging light. In this embodiment, lens 613 collimates the rays 613. In other embodiments a collimated source may be used. Additional embodiments may uses a diffusing element following the source in order to homogenize the spatial mode profile of the source.

There are three distinct advantages to wafer alignment: First, during training the operator can always view the wafer "right-side-up," e.g., with the notch in the direction towards the bottom of the view screen. This makes training of the system easier. Second, pattern recognition is more difficult with arbitrary orientations of the wafer. The better the initial alignment, the easier is pattern recognition. Third, the pinhole can have a square cross section (perpendicular to the measurement or monitor beams), which allows for greater light transmittance without an increase in the minimum box size that can be used for the measurement.

Embodiments of this wafer metrology device may be integrated into a wafer processor. As described above, different embodiments of this wafer metrology device allow it to be at different positions relative to the wafer under test. Particular embodiments utilize raiser and feeder elements to take wafers from other locations and introduce them to an apparatus according to this wafer metrology device.

Figure 18:
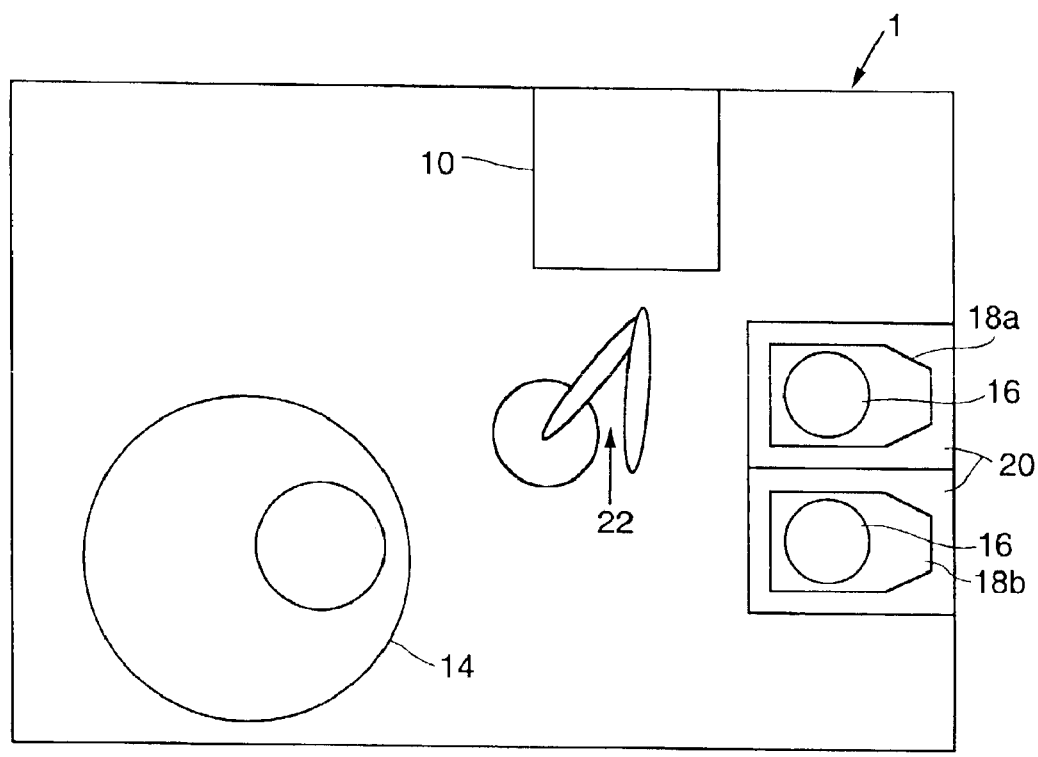
FIG. 18 illustrates one embodiment of an integrated metrology apparatus.

FIG. 18 shows a preferred embodiment integrated with a wafer process station in a fabrication line. For purposes of illustration and not limitation, the process station in the embodiment in FIG. 18 is a polisher. A polishing machine 1 and an integrated surface metrology station, ISMS 10, are shown. The polishing machine 1 comprises a polishing unit 14, loading areas 18 and transport system 22. In addition wafers 16 in carriers 18 are shown. As shown in FIG. 18, the metrology station is apart from the process station and coupled to the process station.

Wafers 16 are brought to and taken from polishing machine 1 in carriers 18 through loading areas 20. The carriers may be cassettes or FOUPs, terms common in the art. Transport system 22 is a device or set of devices for transporting the wafers within polisher 1. Specific embodiments may comprise a robot, such as the EquipeWTM-105. The transport system can move the wafers to any of the carriers 18, the polishing unit 14 or the ISMS 10.

In many CMP applications, the CMP machine is dry-in/wet-out. After leaving the CMP machine, the wafers go to a cleaner/dryer, which is wet-in/dry-out. After going through the cleaner/dryer, the wafers can be measured on a standard standalone, dry metrology system. If there is not an integrated, wet metrology system on the CMP machine, then there is a long delay between polishing the wafer and the first time it can be measured in detail, to see if the CMP process is performing well. This delay is undesirable, since it reduces the ability to tightly control the process with information from wafers that have just been polished.

In situations as described above, a wet standalone metrology system reduces the delay and improves the ability to control the CMP process. This is an attractive option in a number of situations, i.e.,
1. where there is an installed base of CMP machines which cannot be retrofitted with integrated metrology.
2. where the cost of fitting multiple CMP machines with integrated metrology is prohibitive, and one standalone machine can service multiple CMP machines. The new process flow according to the present invention comprises acts of 1) polishing, 2) measuring the wafers while wet, and 3) cleaning and drying. The wet wagers require a special wet metrology system to avoid the deleterious effects of water, especially in the form of droplets, on the measurement or measurement system.

A wet standalone system according to this invention should keep the wafers substantially wet while they are on the system. In typical embodiments, a cassette of wafers would be placed on the system. While one or more wafers are being measured, the rest of the wafers in the cassette should not substantially dry off, because the wafers are wet with slurry that may form a 'cement' on the wafer if allowed to dry. A standalone system according to this invention accomplishes this either by immersing the wafers or misting them, in respective embodiments. In an embodiment including an immersion system, the wafers in a cassette may be held in tank. If the wafers are horizontal or at an angle near horizontal, the cassette may be raised and lowered to allow robot access to wafers while keeping them wet. An angle near horizontal is preferable to horizontal to reduce the hydrodynamic forces of raising and lowering the wafers, and to help keep the wafers fully inserted in the cassette. If the wafers are either vertical or at an angle near vertical, hydrodynamic forces may be reduced to a minimum, the tendency for wafers to 'float' out of the cassette may be eliminated, and it may be possible for the robot to pick and place wafers without raising the cassette out of the water.

According to this invention, there are several embodiments for handling the wafers. In a particular embodiment, the wet wafers are loaded manually into the wet metrology unit, e.g., with a vacuum wand. Alternate embodiments have a robot, which extracts the wafers from the cassette, and returns them. In further embodiments, a cart that is used to transport wet wafers docks onto the metrology system, and the robot lifts the wafers out of the cassette, which may be still on the cart. The cart may be a manual or robotic cart.

According to this invention, the metrology of a particular embodiment may be any metrology that is relevant to the CMP process. In embodiments for dielectric CMP, film-thickness metrology is included. In embodiments for STI and metal CMP, dishing and erosion metrology is included. In embodiments for ILD CMP, detection of puddling is included. In most embodiments, defect detection is included.

In most embodiments, short-time, detailed feedback is provided when the system is being brought up after a pad change or any maintenance. In these embodiments, monitor wafers are used to gather information. Shortening the delay between polishing and measurement according to these aspects of the invention decreases the down time and improves overall equipment effectiveness (OEE).

The foregoing description of various embodiments of the invention has been presented for purposes of illustration and description. It is not intended to limit the invention to the precise forms disclosed. Many modifications and equivalent arrangements will be apparent.

What is claimed is:

1. An apparatus for evaluating a predetermined region of a sample, said apparatus comprising:

a solid state light source for illuminating the sample;

a first camera for capturing a first image of the sample, illuminated by the solid state light source, in order to identify a location of the predetermined region to be measured;

a second light source for illuminating the predetermined region;

a detector for measuring light from the second light source that is reflected from the predetermined region; and a second camera for capturing a second image of the sample in order to identify the location of the predetermined region to be measured.

2. An apparatus as recited in claim 1, wherein the second camera has a smaller field of view than the first camera.

3. An apparatus as recited in claim 1, wherein the second camera captures a second image of the sample while the sample is illuminated by the second light source.

* * * * *